(12) United States Patent
Kimura et al.

(10) Patent No.: US 7,692,026 B2
(45) Date of Patent: Apr. 6, 2010

(54) PYRROLOTRIAZOLE COMPOUND

(75) Inventors: Keizo Kimura, Kanagawa (JP); Fumio Iwamoto, Kanagawa (JP); Mitsuo Yoshikane, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/235,379

(22) Filed: Sep. 27, 2005

(65) Prior Publication Data
US 2006/0068336 A1    Mar. 30, 2006

(30) Foreign Application Priority Data
Sep. 27, 2004    (JP)    ............... 2004-280460

(51) Int. Cl.
C07D 487/04    (2006.01)
(52) U.S. Cl. .................. 548/262.4; 430/384
(58) Field of Classification Search .............. 548/262.4; 430/384
See application file for complete search history.

(56) References Cited

U.S. PATENT DOCUMENTS

| | | | |
|---|---|---|---|
| 5,256,526 A | 10/1993 | Suzuki et al. | |
| 6,132,945 A | 10/2000 | Saito et al. | |
| 6,773,875 B2 * | 8/2004 | Nakamine et al. | ........... 430/552 |
| 2001/0004512 A1 | 6/2001 | Yoshioka et al. | |

FOREIGN PATENT DOCUMENTS

| | | |
|---|---|---|
| EP | 0 714 892 A1 | 6/1996 |
| EP | 0 883 024 A1 | 12/1998 |
| EP | 0 932 079 A1 | 7/1999 |
| EP | 1 193 548 A2 | 4/2002 |
| JP | 8-109172 A | 4/1996 |

OTHER PUBLICATIONS

Organic Chemistry, 2nd edition, John McMurry p. 64.*
Vippagunta et al., Advanced Drug Delivery Reviews, p. 1.*
Vippagunta et al., Advanced Drug Reviews, 48 (2001), pp. 5-26.*
Full machine English translation of Japanese Patent Publication No. 2004-123553, published Apr. 22, 2004.
Full machine English translation of Japanese Patent Publication No. 2002-174885, published Jun. 21, 2002.

* cited by examiner

*Primary Examiner*—Yong Chu
(74) *Attorney, Agent, or Firm*—Birch, Stewart, Kolasch & Birch, LLP

(57) ABSTRACT

Disclosed is a pyrrolotriazole compound represented by the following formula (I) and having an organic compound incorporated into crystals thereof or a pyrrolotriazole compound represented by the following formula (II) and having an alcohol incorporated into crystals thereof.

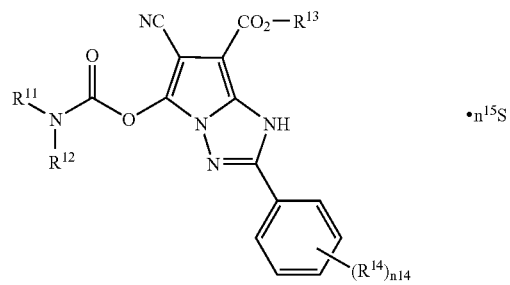

Formula (I)

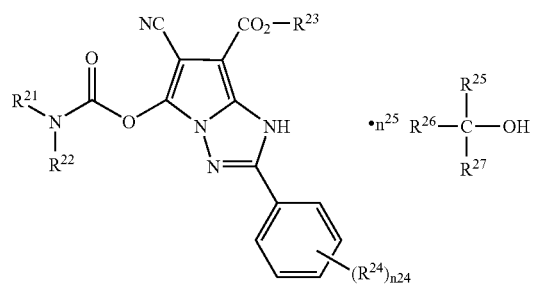

Formula (II)

1 Claim, 1 Drawing Sheet

PYRROLOTRIAZOLE COMPOUND

CROSS-REFERENCE TO RELATED APPLICATION

This application claims priority under 35 USC 119 from Japanese Patent Application No. 2004-280460, the disclosure of which is incorporated herein by reference.

BACKGROUND OF THE INVENTION

1. Field of the Invention

The present invention relates to a novel pyrrolotriazole compound, and particularly, to a pyrrolotriazole compound useful as synthetic raw materials of dyes and dye forming couplers, especially, cyan couplers for silver halide color photosensitive materials.

2. Description of the Related Art

The fact that pyrrolotriazole compounds are useful as cyan couplers for silver halide color photosensitive materials is known from, for example, Japanese Patent Application Laid-Open (JP-A) Nos. 5-31,3324 and 2002-174885. Also, these pyrrolotriazole compounds are useful as raw materials as synthetic intermediates for azomethine dyes and dye forming couplers.

However, when the production of these pyrrolotriazole compounds is considered, the production methods heretofore disclosed in JP-A Nos. 8-109172 and 2004-123553, are unsatisfactory from the standpoint of operation. Although an improvement in crystallinity, filtering characteristics and drying aptitude, and among these especially improvement in filtering characteristics, has been earnestly desired, no specific and satisfactory method of solving the above problem has been known.

Accordingly, development of a novel pyrrolotriazole compound which is useful as synthetic raw materials of dyes and as dye forming couplers, especially cyan couplers for silver halide color photosensitive materials, and has superior filtering characteristics has been desired.

SUMMARY OF THE INVENTION

The present invention has been made in view of the above circumstances and provides a novel compound having an organic solvent incorporated into the following pyrrolotriazole compound.

A first aspect of the present invention is to provide a pyrrolotriazole compound represented by the following formula (I) and having an organic compound incorporated into crystals thereof Formula (I)

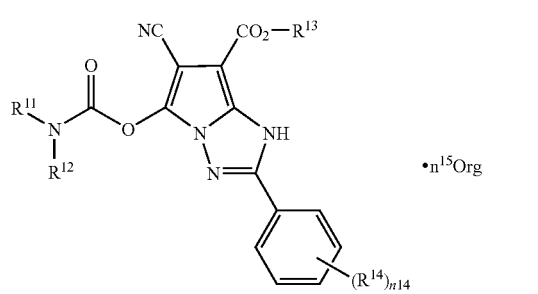

wherein $R^{11}$ and $R^{12}$ each independently represent an aliphatic group, an aromatic group or a heterocyclic group; $R^{11}$ and $R^{12}$ may be combined with each other to form a five-membered or six-membered nitrogen-containing hetero ring; $R^{13}$ represents an aliphatic group; $R^{14}$ represents a substituent; Org represents an organic compound having at least one carbon atom; $n^{14}$ denotes an integer from 0 to 5; when $n^{14}$ is 2 or more, $R^{14}$s may be the same or different and may be combined with each other to form a ring; and $n^{15}$ denotes a positive number.

A second aspect of the present invention is to provide a pyrrolotriazole compound represented by the following formula (II) and having an alcohol incorporated into crystals thereof:

Formula (II)

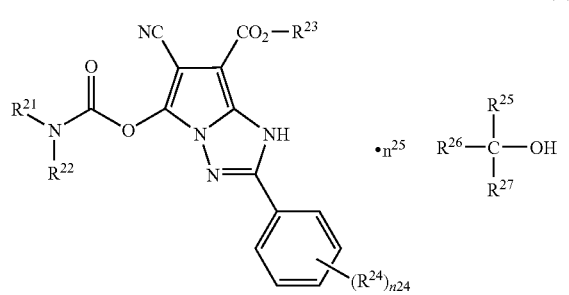

wherein $R^{21}$ and $R^{22}$ each independently represent an aliphatic group, an aromatic group or a heterocyclic group; $R^{21}$ and $R^{22}$ may be combined with each other to form a five-membered or six-membered nitrogen-containing hetero ring; $R^{23}$ represents an aliphatic group; $R^{24}$ represents a substituent; $R^{25}$, $R^{26}$ and $R^{27}$ each independently represent a hydrogen atom, an aliphatic group, an aromatic group or a heterocyclic group; $n^{24}$ denotes an integer from 0 to 5; when $n^{24}$ is 2 or more, $R^{24}$s may be the same or different and may be combined with each other to form a ring; and $n^{25}$ denotes a positive number.

DETAILED DESCRIPTION OF THE INVENTION

Figure 1:
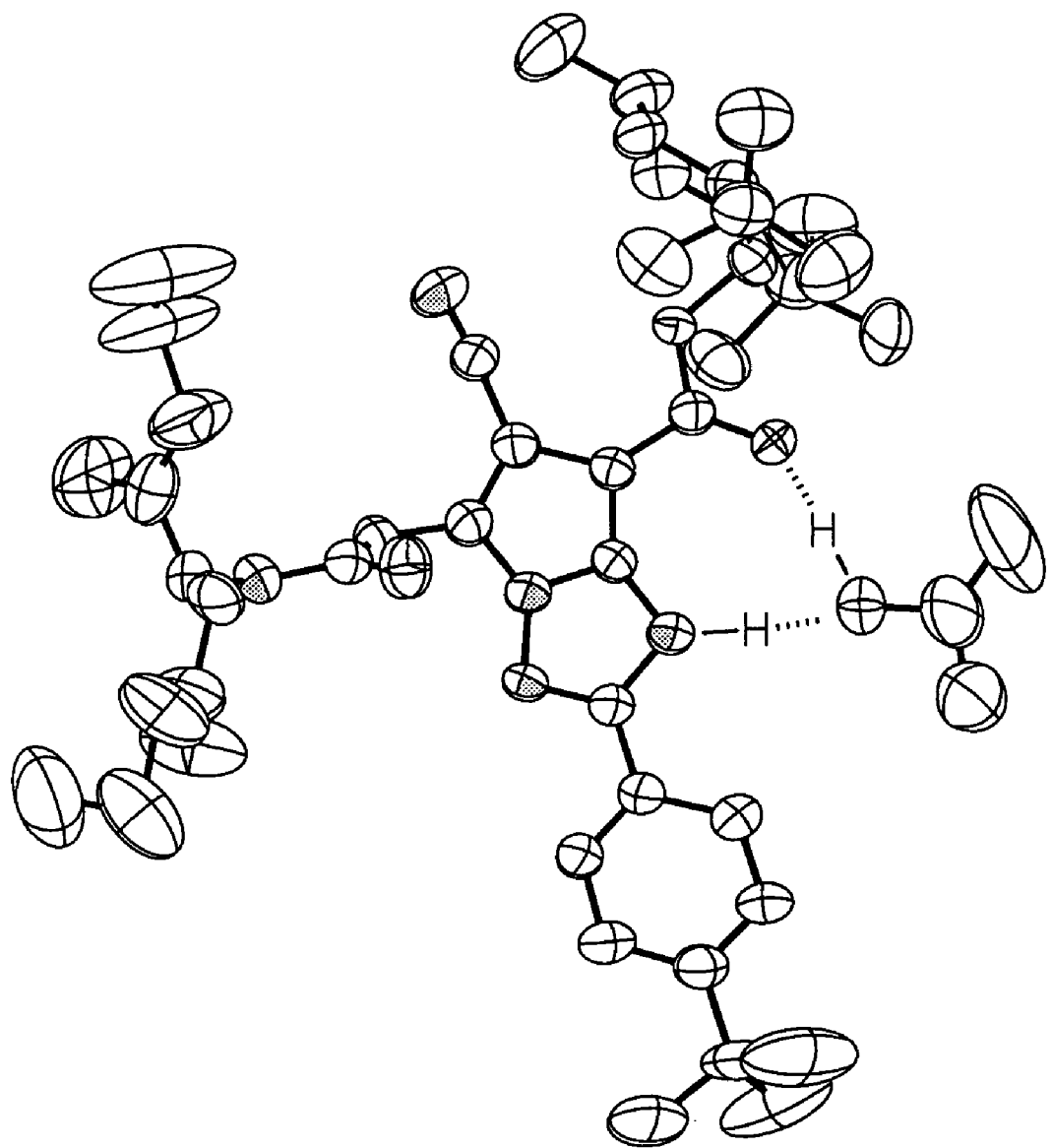
FIG. 1 is an ORTEP drawing showing the three-dimensional structure obtained by X-ray structural analysis of an exemplified compound (C-14) obtained in Example 1.

The present invention will be explained in detail hereinbelow.

1. Explanations of Each Group in the Formula According to the Invention

In this specification, first the aliphatic group means an alkyl group, substituted alkyl group, alkenyl group, substituted alkenyl group, alkinyl group, substituted alkinyl group, aralkyl group or substituted aralkyl group. The alkyl group may be branched and may form a ring (specifically, for example, a cycloalkyl group, cycloalkenyl group and cycloalkinyl group). The number of atoms of the alkyl group is preferably 1 to 20 and more preferably 1 to 18. The alkyl part of the substituted alkyl group is the same as the above alkyl group. The alkenyl group may be branched and may form a ring. The number of atoms of the alkenyl group is preferably 2 to 20 and more preferably 2 to 18. The alkenyl part of the substituted alkenyl group is the same as the above alkenyl group. The alkinyl group may be branched and may form a ring. The number of atoms of the alkinyl group is preferably 2 to 20 and more preferably 2 to 18. The alkinyl part of the substituted alkinyl group is the same as the above alkinyl group. Each alkyl part of the aralkyl group and substituted aralkyl group is the same as the above alkinyl group. Each aryl part of the aralkyl group and substituted aralkyl group is the same as the aryl group which will be described later.

Examples of the substituent of the alkyl part of the substituted alkyl group, substituted alkenyl group, substituted alkinyl group and substituted aralkyl group include a halogen atom (e.g., a chlorine atom, bromine atom and iodine atom), alkyl group (represents a straight-chain, branched or cyclic substituted or unsubstituted alkyl group they include an alkyl group (preferably an alkyl group having 1 to 30 carbon atoms, for example, methyl, ethyl, n-propyl, isopropyl, t-butyl, n-octyl, eicosyl, 2-chloroethyl, 2-cyanoethyl and 2-ethylhexyl), cycloalkyl group (preferably a substituted or unsubstituted cycloalkyl group having 3 to 30 carbon atoms, for example, cyclohexyl, cyclopentyl and 4-n-dodecylcyclohexyl) and, bicyloalkyl group (preferably a bicycloalkyl group having 5 to 30 carbon atoms, specifically a monovalent group obtained by removing one hydrogen atom from bicyloalkane having 5 to 30 carbon atoms, for example, bicyclo[1,2,2]heptane-2-yl and bicyclo[2,2,2]octane-3-yl) and a tricyclo structure having more cyclic structures. The alkyl groups (for example, the alkyl group of an alkylthio group) in the substituent explained below represents an alkyl group having such a concept.), alkenyl group (represents a straight-chain, branched or cyclic substituted or unsubstituted alkenyl group. They include an alkenyl group (preferably a substituted or unsubstituted alkenyl group having 2 to 30 carbon atoms, for example, vinyl, allyl, pulenyl, geranyl and oleyl), cycloalkenyl group (preferably a substituted or unsubstituted cycloalkenyl group having 3 to 30 carbon atoms, namely, a monovalent group obtained by removing one hydrogen atom from a cycloalkene having 3 to 30 carbon atoms, for example, 2-cyclopentene-1-yl and 2-cyclohexene-1-yl) and bicycloalkenyl group (a substituted or unsubstituted bicycloalkenyl group and preferably a substituted or unsubstituted bicycloalkenyl group having 5 to 30 carbon atoms, specifically, a monovalent group obtained by removing one hydrogen atom from a cycloalkene having one double bond, for example, bicyclo[2,2,1]hepto-2-ene-1-yl and bicyclo[2,2,2]octo-2-ene-4-yl)), alkinyl group (preferably a substituted or unsubstituted alkinyl group having 2 to 30 carbon atoms, for example, ethynyl, propalgyl and trimethylsilylethynyl group;

aryl group (preferably a substituted or unsubstituted aryl group, for example, phenyl, p-tolyl, naphthyl, m-chlorophenyl and o-hexadecanoylaminophenyl), heterocyclic group (preferably a monovalent group obtained by removing one hydrogen atom from a five- or six-membered substituted or unsubstituted aromatic or non-aromatic heterocyclic compound and more preferably a five- or six-membered aromatic heterocyclic group having 3 to 30 carbon atoms, for example, 2-furyl, 2-thienyl, 2-pyrimidinyl and 2-benzothiazolyl), cyano group, hydroxyl group, nitro group, carboxyl group, alkoxy group (preferably a substituted or unsubstituted alkoxy group having 1 to 30 carbon atoms, for example, methoxy, ethoxy, isopropoxy, t-butoxy, n-octyloxy and 2-methoxyethoxy), aryloxy group (preferably a substituted or unsubstituted aryloxy group having 6 to 30 carbon atoms, for example, phenoxy, 2-methylphenoxy, 4-t-butylphenoxy, 3-nitrophenoxy and 2-tetradecanoylaminophenoxy), silyloxy group (preferably a silyloxy group having 3 to 20 carbon atoms, for example, trimethylsilyloxy and t-butyldimethylsilyloxy), heterocyclic oxy group (preferably a substituted or unsubstituted heterocyclic oxy group having 2 to 30 carbon atoms, for example, 1-phenyltetrazole-5-oxy and 2-tetrahydropyranyloxy), acyloxy group (preferably a formyloxy group, substituted or unsubstituted alkylcarbonyloxy group having 2 to 30 carbon atoms or a substituted or unsubstituted arylcarbonyloxy group having 6 to 30 carbon atoms, for example, formyloxy, acetyloxy, pivaloyloxy, stearoyloxy, benzoyloxy and p-methoxyphenylcarbonyloxy);

carbamoyloxy group (preferably a substituted or unsubstituted carbamoyloxy group having 1 to 30 carbon atoms, for example, N,N-dimethylcarbamoyloxy, N,N-diethylcarbamoyloxy, morpholinocarbonyloxy, N,N-di-n-octylaminocarbonyloxy and N-n-octylcarbamoyloxy), alkoxycarbonyloxy group (preferably a substituted or unsubstituted alkoxycarbonyloxy group having 2 to 30 carbon atoms, for example, methoxycarbonyloxy, ethoxycarbonyloxy, t-butoxycarbonyloxy and n-octylcarbonyloxy), aryloxycarbonyloxy group (preferably a substituted or unsubstituted aryloxycarbonyloxy group having 7 to 30 carbon atoms, for example, phenoxycarbonyloxy, p-methoxyphenoxycarbonyloxy and p-n-hexadecyloxyphenoxycarbonyloxy), amino group (preferably an amino group, substituted or unsubstituted alkylamino group having 1 to 30 carbon atoms or substituted or unsubstituted anilino group having 6 to 30 carbon atoms, for example, amino, methylamino, dimethylamino, anilino, N-methyl-anilino and diphenylamino), acylamino group (preferably a formylamino group, substituted or unsubstituted alkylcarbonylamino group having 1 to 30 carbon atoms or substituted or unsubstituted arylcarbonylamino group having 6 to 30 carbon atoms, for example, formylamino, acetylamino, pivaloylamino, lauroylamino, benzoylamino and 3,4,5-tri-n-octyloxyphenylcarbonylamino);

aminocarbonylamino group (preferably a substituted or unsubstituted aminocarbonylamino group having 1 to 30 carbon atoms, for example, carbamoylamino, N,N-dimethylaminocarbonylamino, N,N-diethylaminocarbonylamino and morpholinocarbonylamino), alkoxycarbonylamino group (preferably a substituted or unsubstituted alkoxycarbonylamino group having 2 to 30 carbon atoms, for example, methoxycarbonylamino, ethoxycarbonylamino, t-butoxycarbonylamino, n-octadecyloxycarbonylamino, N-methyl-methoxycarbonylamino), aryloxycarbonylamino group (preferably a substituted or unsubstituted aryloxycarbonylamino group having 7 to 30 carbon atoms, for example, phenoxycarbonylamino, p-chlorophenoxycarbonylamino and m-n-octyloxyphenoxycarbonylamino), sulfamoylamino group (preferably a substituted or unsubstituted sulfamoylamino group having 0 to 30 carbon atoms, for example, sulfamoylamino, N,N-dimethylaminosulfonylamino and N-n-octylaminosulfonylamino), alkyl or arylsulfonylamino group (preferably a substituted or unsubstituted alkylsulfonylamino group having 1 to 30 carbon atoms or a substituted or unsubstituted arylsulfonylamino group having 6 to 30 carbon atoms, for example, methylsulfonylamino, butylsulfonylamino, phenylsulfonylamino, 2,3,5-trichlorophenylsulfonylamino and p-methylphenylsulfonylamino), mercapto group, alkylthio group (preferably a substituted or unsubstituted alkylthio group having 1 to 30 carbon atoms, for example, methylthio, ethylthio and n-hexadecylthio), arylthio group (preferably a substituted or unsubstituted arylthio group having 6 to 30 carbon atoms, for example, phenylthio, p-chlorophenylthio and m-methoxyphenylthio), heterocyclic thio group (preferably a substituted or unsubstituted heterocyclic thio group having 2 to 30 carbon atoms, for example, 2-benzothiazolylthio and 1-phenyltetrazole-5-ylthio);

sulfamoyl group (preferably a substituted or unsubstituted sulfamoyl group having 0 to 30 carbon atoms, for example, N-ethylsulfamoyl, N-(3-dodecyloxypropyl)sulfamoyl, N,N-dimethylsulfamoyl, N-acetylsulfamoyl, N-benzoylsulfamoyl, N-(N-orderǀphenylcarbamoyl) sulfamoyl), sulfo group, alkyl or arylsulfinyl group (preferably a substituted or unsubstituted alkylsulfinyl group having 1 to 30 carbon atoms or arylsulfinyl group having 6 to 30 carbon atoms, for example, methylsulfinyl, ethylsulfinyl, phenylsulfinyl and p-methylphenylsulfinyl), alkyl or arylsulfonyl group (preferably a substituted or unsubstituted alkylsulfonyl group having 1 to 30 carbon atoms or arylsulfonyl group having 6 to 30 carbon atoms, for example, methylsulfonyl, ethylsulfonyl, phenylsulfonyl and p-methylphenylsulfonyl);

acyl group (preferably a formyl group, a substituted or unsubstituted alkylcarbonyl group having 2 to 30 carbon atoms, substituted or unsubstituted arylcarbonyl group having 7 to 30 carbon atoms or heterocyclic carbonyl group which has 4 to 30 carbon atoms and in which the ring is connected with the carbonyl group through a carbon atom, for example, acetyl, pivaloyl, 2-chloroacetyl, stearoyl, benzoyl, p-n-octyloxyphenylcarbonyl, 2-pyridylcarbonyl and 2-furylcarbonyl), aryloxycarbonyl group (preferably a substituted or unsubstituted aryloxycarbonyl group having 7 to 30 carbon atoms, for example, phenoxycarbonyl, o-chlorophenoxycarbonyl, m-nitrophenoxycarbonyl and p-t-butylphenoxycarbonyl), alkoxycarbonyl group (preferably a substituted or unsubstituted alkoxycarbonyloxy group having 2 to 30 carbon atoms, for example, methoxycarbonyl, ethoxycarbonyl, t-butoxycarbonyl and n-octadecyloxycarbonyl), carbamoyl group (preferably a substituted or unsubstituted carbamoyl group having 1 to 30 carbon atoms, for example, carbamoyl, N-methylcarbamoyl, N,N-dimethylcarbamoyl, N,N-di-n-octylcarbamoyl and N-(methylsulfonyl)carbamoyl), aryl or heterocyclic azo group (preferably a substituted or unsubstituted aryl azo group having 6 to 30 carbon atoms or heterocyclic azo group, for example, phenylazo, p-chlorophenylazo and 5-ethylthio-1,3,4-thiadiazole-2-ylazo), imide group (preferably N-succinimide and N-phthalimide), phosphino group (preferably a substituted or unsubstituted phosphino group having 2 to 30 carbon atoms, for example, dimethylphosphino, diphenylphosphino and methylphenoxyphosphino), phosphinyl group (preferably a substituted or unsubstituted phosphinyl group having 2 to 30 carbon atoms, for example, phosphinyl, dioctyloxyphosphinyl and diethoxyphosphinyl), phosphinyloxy group (preferably a substituted or unsubstituted phosphinyloxy group having 2 to 30 carbon atoms, for example, diphenoxyphosphinyloxy and dioctyloxyphosphinyloxy), phosphinylamino group (preferably a substituted or unsubstituted phosphinylamino group having 2 to 30 carbon atoms, for example, dimethoxyphosphinylamino and dimethylaminophosphinylamino) and silyl group (preferably a substituted or unsubstituted alkoxycarbonyloxy group having 2 to 30 carbon atoms, for example, trimethylsilyl, t-butyldimethylsilyl and phenyldimethylsilyl).

Among the above functional groups, those having a hydrogen atom may be substituted with the above group at the position where the hydrogen atom is removed. Examples of such a functional group include an alkylcarbonylaminosulfonyl group, arylcarbonylaminosulfonyl group, alkylsulfonylaminocarbonyl group and arylsulfonylaminocarbonyl group. Specific examples of these groups include methylsulfonylaminocarbonyl, p-methylphenylsulfonylaminocarbonyl, acetylaminosulfonyl and benzoylaminosulfonyl.

Examples of the substituent of the aryl part of the substituted aralkyl group are the same as the examples of the substituent of the following substituted aryl group.

In this specification, the aromatic group means an aryl group or a substituted aryl group. These aromatic groups may be condensed with aliphatic rings, other aromatic rings or hetero rings. The number of carbons of the aromatic group is preferably 6 to 40, more preferably 6 to 30 and still more preferably 6 to 20. Among these groups, the aryl group is preferably phenyl or naphthyl and particularly preferably phenyl.

The aryl part of the substituted aryl group is the same as that of the above aryl group. Examples of the substituent of the substituted aryl group are the same as those given as the examples of the substituent of the alkyl part of the aforementioned substituted alkyl group, substituted alkenyl group, substituted alkinyl group and substituted aralkyl group.

In this specification, the hetero ring in the heterocyclic group preferably include a five- or six-membered saturated or unsaturated hetero ring. This hetero ring may be condensed with aliphatic rings, aromatic rings or other hetero rings. Examples of the hetero atom of the hetero ring include B, N, O, S, Se and Te. N, O or S is preferable as the hetero atom. The hetero ring preferably contains a carbon atom having a free atomic valence (monovalent) (the heterocyclic group is combined through the carbon atom). The number of atoms of the heterocyclic group is preferably 1 to 40, more preferably 1 to 30 and still more preferably 1 to 20. Examples of the saturated hetero ring in the heterocyclic group include a pyrrolidine ring, morpholine ring, 2-bora-1,3-dioxolan ring and 1,3-thiazolidine ring. Examples of the unsaturated hetero ring in the heterocyclic group include an imidazole ring, thiazole ring, benzothiazole ring, benzoxazole ring, benzotriazole ring, benzoselenazole, pyridine ring, pyrimidine ring and quinoline ring. The heterocyclic group may have a substituent. Examples of the substituent are the same as those given as the examples of the substituent of the alkyl part of the aforementioned substituted alkyl group, substituted alkenyl group, substituted alkinyl group and substituted aralkyl group.

2. Explanations of the Compound Represented by the Formula (I) or (II)

Next, the compound represented by the formula (I) or (II) will be explained. The compound represented by the formula (I) or (II) has excellent filterability and operating ability.

1) Explanations of the Compound Represented by the Formula (I)

$R^{11}$ and $R^{12}$ in the formula (I) each independently represent an aliphatic group, an aromatic group or a heterocyclic group, where these groups are the same as those mentioned above. $R^{11}$ and $R^{12}$ may be combined with each other to form a five- or six-membered nitrogen-containing hetero ring.

$R^{11}$ and $R^{12}$ are each independently preferably an aliphatic group or an aromatic group, more preferably an aliphatic group having 1 to 12 carbon atoms or an aromatic group having 6 to 12 carbon atoms. $R^{11}$ and $R^{12}$ are each independently preferably an aliphatic group unsubstituted or substituted with a halogen atom, aryl group, heterocyclic group, cyano group, hydroxyl group, nitro group, alkoxy group, aryloxy group, silyloxy group, heterocyclic oxy group, acyloxy group, carbamoyloxy group, alkoxycarbonyloxy group, aryloxycarbonyloxy group, amino group, acylamino group, aminocarbonylamino group, alkoxycarbonylamino group, aryloxycarbonylamino group, sulfamoylamino group, alkyl or arylsulfonylamino group, mercapto group, alkyl or arylthio group, heterocyclic thio group, sulfamoyl group, alkyl or arylsulfinyl group, alkyl or arylsulfonyl group, acyl group, alkoxycarbonyl group, aryloxycarbonyl group, carbamoyl group, imide group, phosphino group, phosphinyl group, phosphinyloxy group, phosphinylamino group or silyl group, or an aromatic group unsubstituted or substituted with a halogen atom, alkyl group, alkenyl group, alkinyl group, heterocyclic group, cyano group, hydroxyl group, nitro group, alkoxy group, aryloxy group, silyloxy group, heterocyclic oxy group, acyloxy group, carbamoyloxy group, alkoxycarbonyloxy group, aryloxycarbonyloxy group, amino group, acylamino group, aminocarbonylamino group, alkoxycarbonylamino group, aryloxycarbonylamino group, sulfamoylamino group, alkyl or arylsulfonylamino group, mercapto group, alkyl or arylthio group, heterocyclic thio group, sulfamoyl group, alkyl or arylsulfinyl group, alkyl or arylsulfonyl group, acyl group, alkoxycarbonyl group, aryloxycarbonyl group, carbamoyl group, imide group, phosphino group, phosphinyl group, phosphinyloxy group, phosphinylamino group or silyl group.

It is more preferable that $R^{11}$ and $R^{12}$ be each independently an aliphatic group unsubstituted or substituted with a halogen atom, aryl group, cyano group, hydroxyl group, nitro group, alkoxy group, aryloxy group, acyloxy group, carbamoyloxy group, alkoxycarbonyloxy group, aryloxycarbonyloxy group, alkyl or arylsulfonyl group, acyl group, alkoxycarbonyl group, aryloxycarbonyl group or carbamoyl group, or an aromatic group unsubstituted or substituted with a halogen atom, alkyl group, alkenyl group, cyano group, hydroxyl group, nitro group, alkoxy group, aryloxy group, acyloxy group, carbamoyloxy group, alkoxycarbonyloxy group, aryloxycarbonyloxy group, alkyl or arylsulfonyl group, acyl group, alkoxycarbonyl group, aryloxycarbonyl group or carbamoyl group.

It is still more preferable that $R^{11}$ and $R^{12}$ be each independently a $C_{1-5}$ aliphatic group unsubstituted or substituted with a cyano group, alkoxy group, acyloxy group, carbamoyloxy group, acyl group, alkoxycarbonyl group or carbamoyl group. It is even more preferable that $R^{11}$ and $R^{12}$ be each independently an alkyl group substituted with an alkoxycarbonyl group having 1 to 4 carbon atoms. These functional groups may have a substituent. Examples of the substituent are the same as those given as the examples of the substituent of the alkyl part of the aforementioned substituted alkyl group, substituted alkenyl group, substituted alkinyl group and substituted aralkyl group.

It is most preferable that $R^{11}$ and $R^{12}$ be each independently a methoxycarbonylmethyl group and ethoxycarbonylmethyl group. $R^{11}$ and $R^{12}$ may be combined with each other to form a nitrogen-containing hetero ring.

The following compounds are preferable examples of the group represented by $R^{11}R^{12}N$— which is a partial structure of the formula (I), though the invention is not limited to these examples.

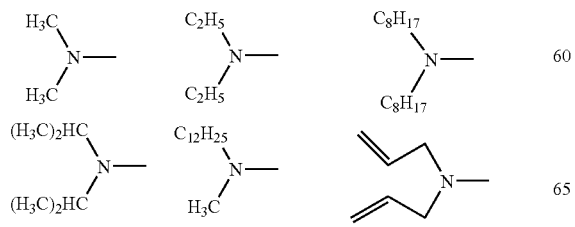

-continued

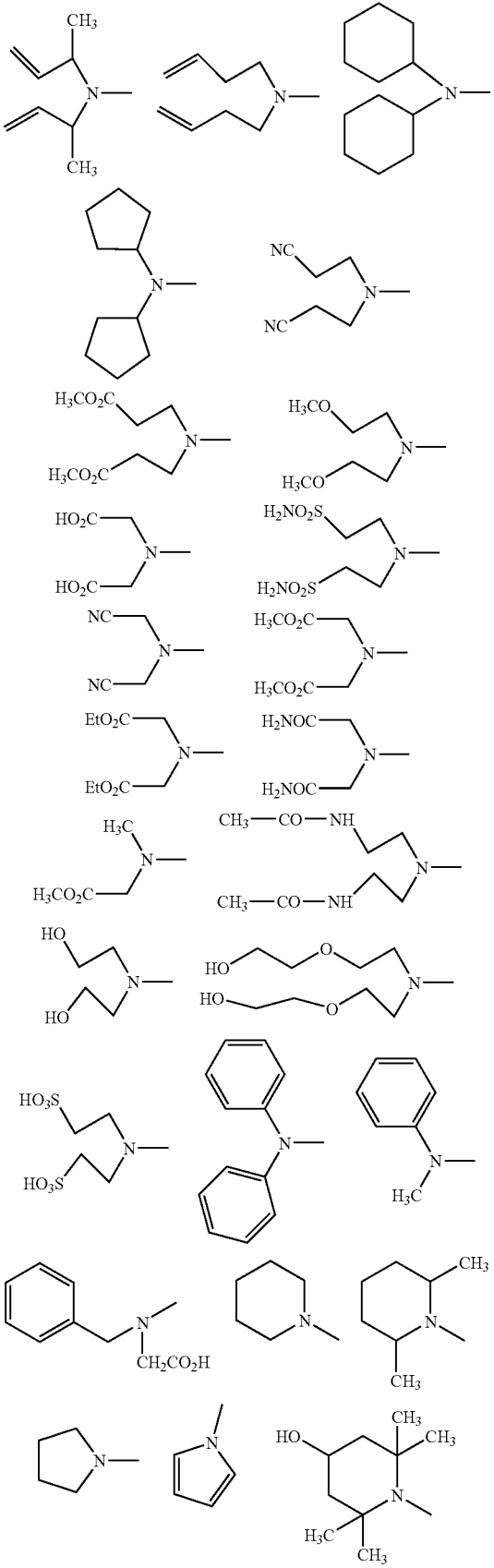

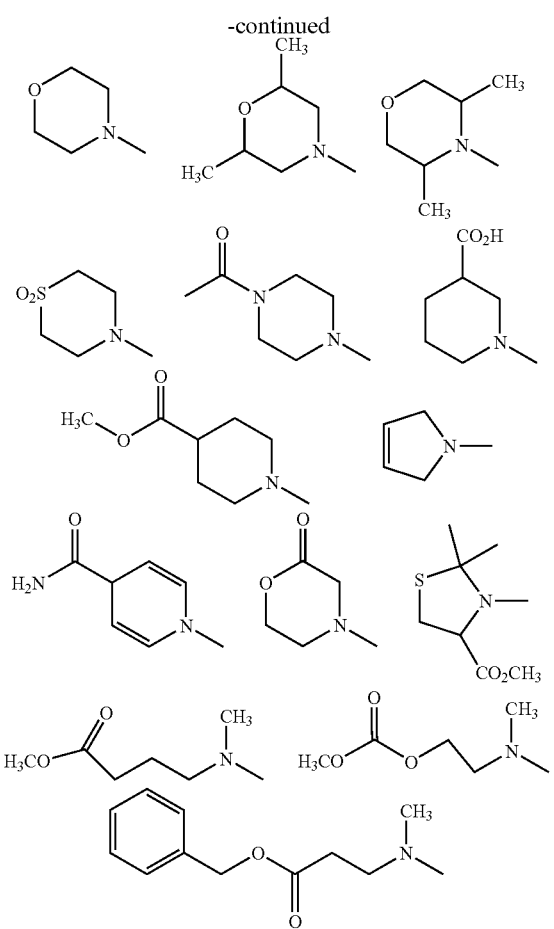

$R^{13}$ represents an aliphatic group and preferable and specific examples of the aliphatic group are the same as those in the case of the above aliphatic group. More preferable examples of the aliphatic group are aliphatic groups having 1 to 30 carbon atoms.

$R^{13}$ is still more preferably a group represented by the following formula (III).

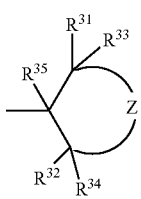

Formula (III)

In the formula (III), $R^{31}$ and $R^{32}$ each independently represent an aliphatic group. Preferable and specific examples of the aliphatic group are the same as those of the aforementioned aliphatic group. $R^{31}$ and $R^{32}$ are each independently preferably an alkyl group having 1 to 6 carbon atoms, more preferably a secondary or tertiary alkyl group having 2 to 4 carbon atoms. The alkyl group may further have a substituent. Examples of the substituent include the same ones as those given as the examples of the aforementioned substituted alkyl group.

It is most preferable that $R^{31}$ and $R^{32}$ be each independently a t-butyl group.

$R^{33}$, $R^{34}$ and $R^{35}$ each independently represent a hydrogen atom or an aliphatic group. When $R^{33}$, $R^{34}$ and $R^{35}$ each independently represent an aliphatic group, specific and preferable examples of the aliphatic group are the same as those given as examples of the aforementioned aliphatic group. $R^{33}$, $R^{34}$ and $R^{35}$ are each independently preferably a hydrogen atom.

Z represents a carbon atom group necessary to form a five- to eight-membered ring wherein this ring may be substituted or may be a saturated ring or unsaturated ring. When this ring has a substituent, examples of the substituent include those exemplified as the substituent of the alkyl part of the aforementioned alkyl group, alkenyl group, alkinyl group or aralkyl group. Z is preferably a unsubstituted one or one having one substituent. When Z has a substituent, the position where the substituent is bound is preferably a para position with respect to the monovalent connector though no particular limitation is imposed on it and the case where the substituent is a methyl group is particularly preferable.

Z is preferably five- to seven-membered ring and most preferably a six-membered ring.

$R^{14}$ represents a substituent and examples of the substituent include those exemplified as the substituent of the alkyl part of the aforementioned alkyl group, alkenyl group, alkinyl group or aralkyl group. $R^{14}$ is preferably a halogen atom, alkyl group, alkenyl group, alkinyl group, aryl group, heterocyclic group, cyano group, hydroxyl group, nitro group, alkoxy group, aryloxy group, silyloxy group, heterocyclic oxy group, acyloxy group, carbamoyloxy group, amino group, acylamino group, aminocarbonylamino group, alkoxycarbonylamino group, mercapto group, alkyl or arylthio group, alkyl or arylsulfonyl group, acyl group, aryloxycarbonyl group, alkoxycarbonyl group and silyl group, more preferably a halogen atom, hydroxyl group, cyano group, alkyl group having 1 to 8 carbon atoms, alkenyl group, alkoxy group, silyloxy group, acyloxy group, carbamoyloxy group, amino group, acylamino group, alkylsulfonyl group, acyl group, alkoxycarbonyl group, silyl group, aryl group having 6 to 8 carbon atoms and aryloxy group, and still more preferably a halogen atom and alkyl group having 1 to 6 carbon atoms and phenyl group. These functional groups may further have a substituent. Examples of the substituent include the same ones as those given as the examples of the substituent of the alkyl part of the aforementioned substituted alkyl group, substituted alkenyl group, substituted alkinyl group and substituted aralkyl group.

$R^{14}$ is most preferably a t-butyl group.

Org represents an organic compound having at least one carbon atom and is preferably a solvent used in production processes such as a reaction process, extraction process and crystallization process. Org is preferably an organic compound having 1 to 12 carbon atoms, for example, alcohols (e.g., methanol, ethanol, isopropyl alcohol, t-butanol, n-octanol, benzyl alcohol and ethylene glycol), phenols (e.g., phenol and o-cresol), amides or ureides (e.g., N,N-dimethylformamide, N,N-dimethylacetamide and 1,3-dimethyl-2-imidazolidinone), ethers (e.g., dimethyl ether, diethyl ether, tetrahydrofuran, 1,4-dioxane and anisole), sulfoxides (e.g., dimethylsulfoxide and diethylsulfoxide), sulfones (e.g., sulforan), ketones (e.g., acetone, methyl ethyl ketone and cyclohexanone), esters (e.g., ethyl acetate and butyl acetate) or nitriles (e.g., acetonitrile). Org is more preferably alcohols, amides or ureides, ketones or nitriles having 1 to 8 carbon atoms. Org is still more preferably alcohols having 1 to 5 carbon atoms and most preferably isopropyl alcohol.

$n^{14}$ denotes an integer from 0 to 5, preferably 0 to 3 and more preferably 0 or 1.

$n^{15}$ denotes a positive number and specifically, the number of mols of the organic compound represented by Org to be incorporated into pyrrolotriazole crystals thereof based on 1 mol of pyrrolotriazole. A preferable value of $n^{15}$ differs depending on the structure of pyrrolotriazole represented by the formula (I), the type of organic compound represented by Org and the production conditions (temperature, time and amount to be added).

2) Explanations of the Compound Represented by the Formula (II)

In the formula (II), $R^{21}$, $R^{22}$, $R^{23}$, $R^{24}$, $n^{24}$ and $n^{25}$ have the same meanings as $R^{11}$, $R^{12}$, $R^{13}$, $R^{14}$, $n^{14}$ and $n^{15}$ each independently and each preferable range is also the same. $R^{25}$, $R^{26}$ and $R^{27}$ each independently represent a hydrogen atom, an aliphatic group, an aromatic group or a heterocyclic group, preferably a hydrogen atom or an aliphatic group, still more preferably a hydrogen atom or an aliphatic group having 1 to 5 carbon atoms and even more preferably a hydrogen atom or an alkyl group having 1 to 3 carbon atoms. It is most preferable that $R^{25}$ be a hydrogen atom and $R^{26}$ and $R^{27}$ be each independently a methyl group.

3. Specific Examples of the Compound

Specific examples of the compound represented by the formula (I) or (II) will be shown below: however, these examples are not intended to be limiting of the invention.

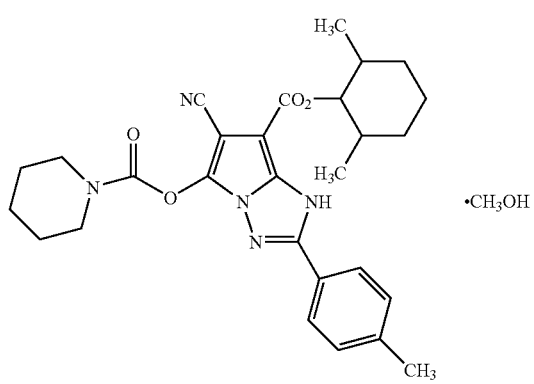

C-1)
·CH$_3$OH

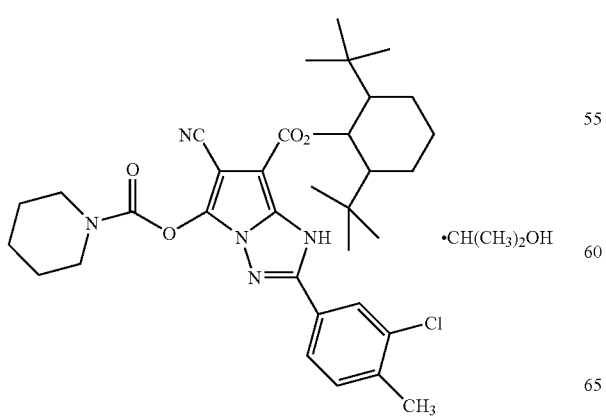

C-2)
·CH(CH$_3$)$_2$OH

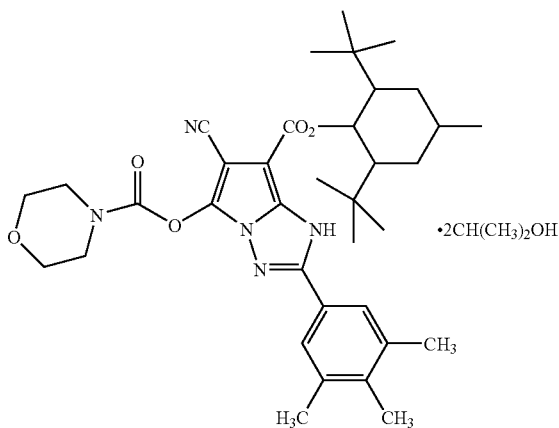

C-3)
·2CH(CH$_3$)$_2$OH

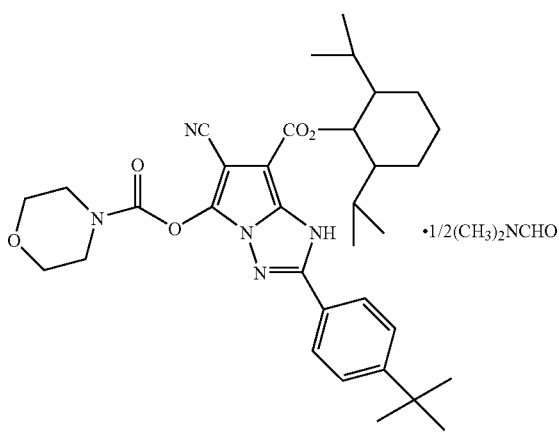

C-4)
·1/2(CH$_3$)$_2$NCHO

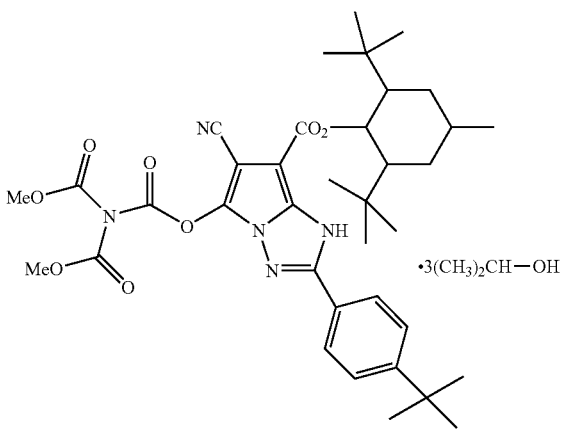

C-5)
·3(CH$_3$)$_2$CH—OH

-continued
C-6)
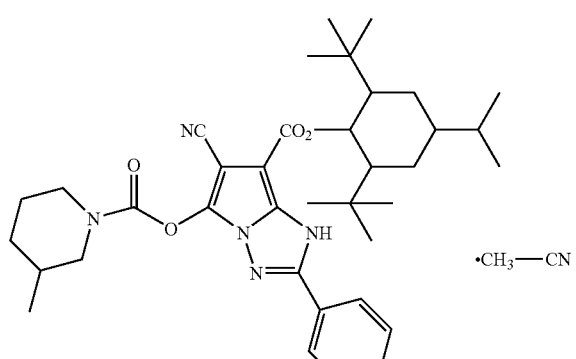
•CH₃—CN
C-7)
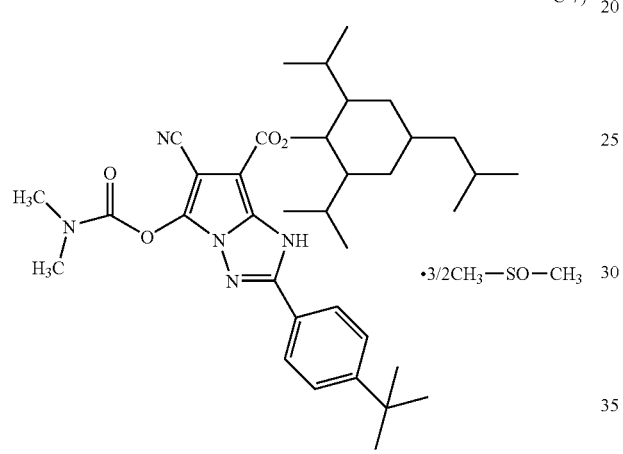
•3/2CH₃—SO—CH₃
C-8)
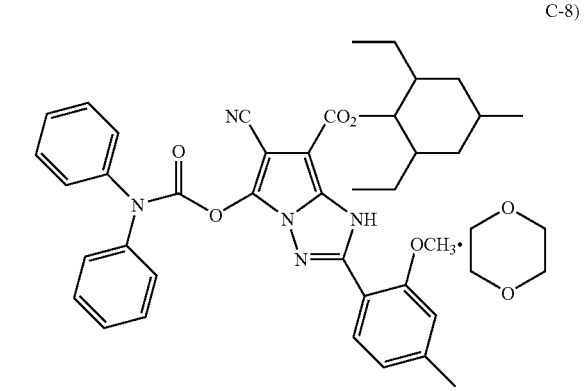
•OCH₃·[dioxane]
C-9)
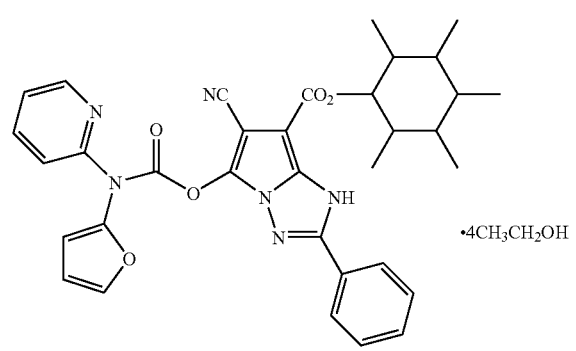
•4CH₃CH₂OH
-continued
C-10)
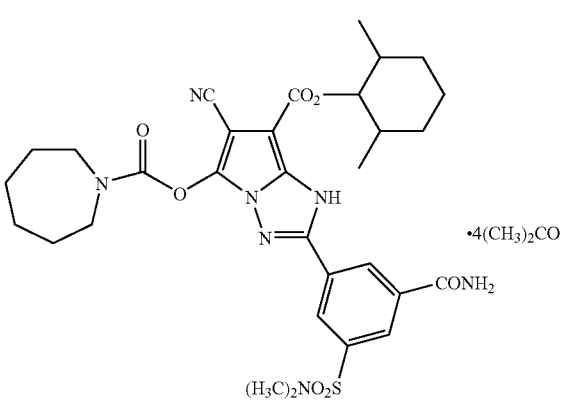
•4(CH₃)₂CO
C-11)
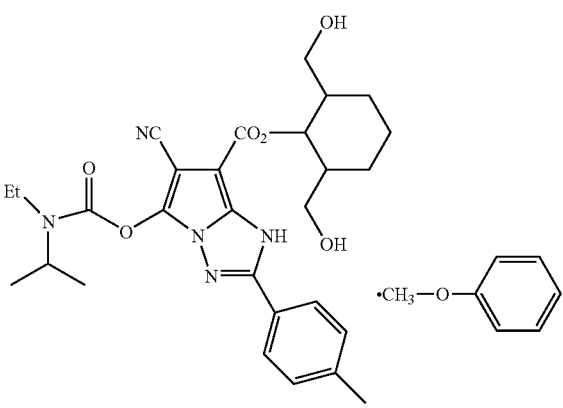
•CH₃—O—[phenyl]
C-12)
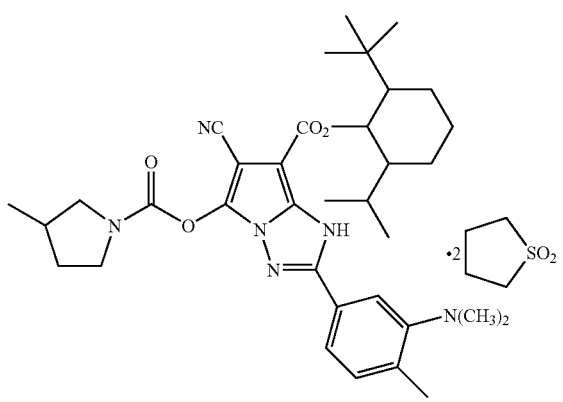
•2 [sulfolane]

C-13)
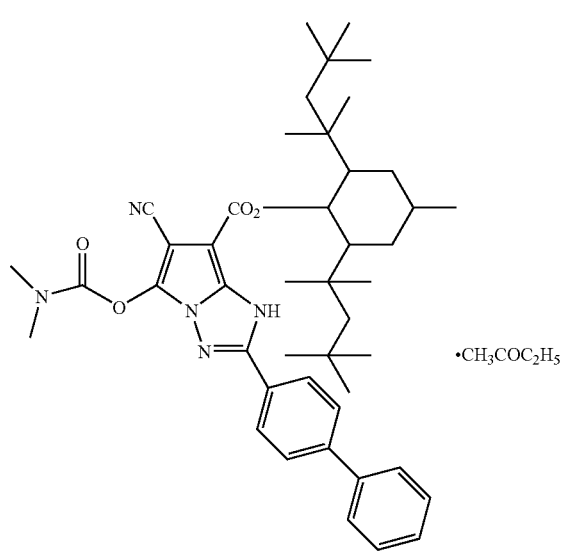
•CH₃COC₂H₅
C-14)
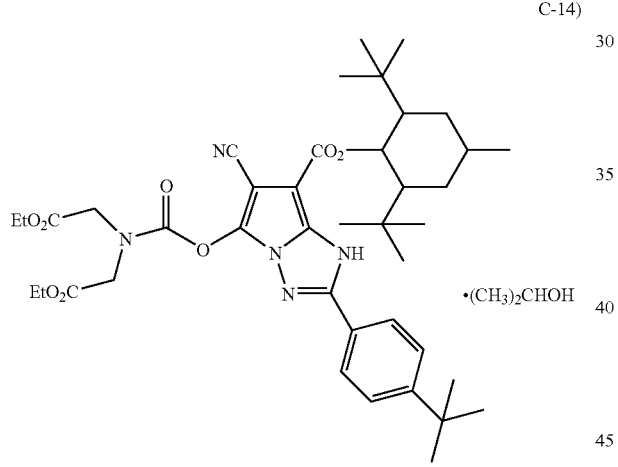
•(CH₃)₂CHOH
C-15)
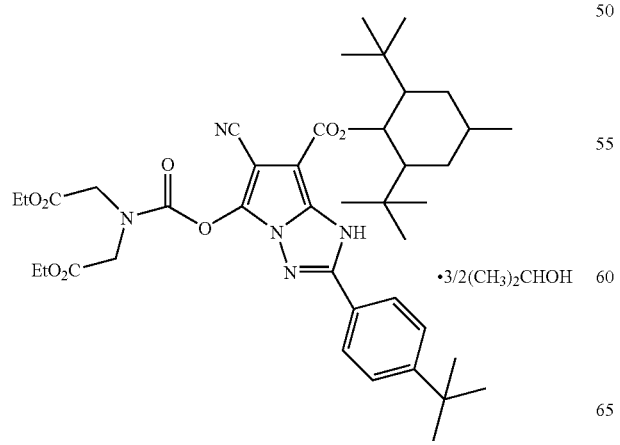
•3/2(CH₃)₂CHOH
C-16)
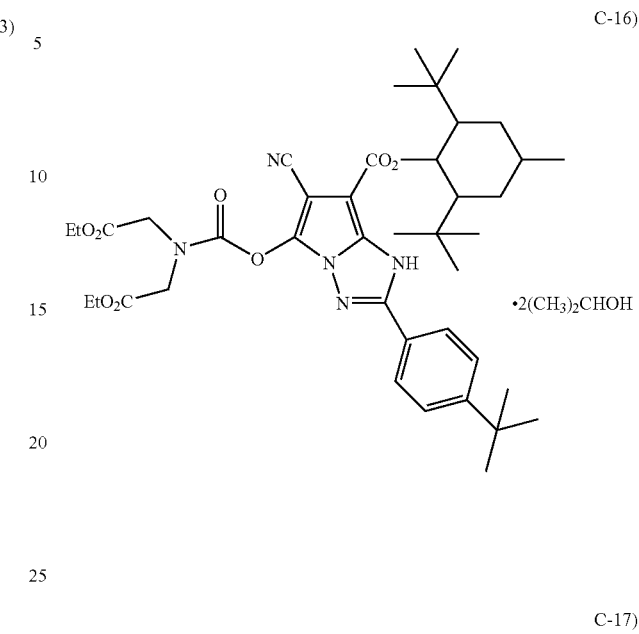
•2(CH₃)₂CHOH
C-17)
•CH₃OH
C-18)
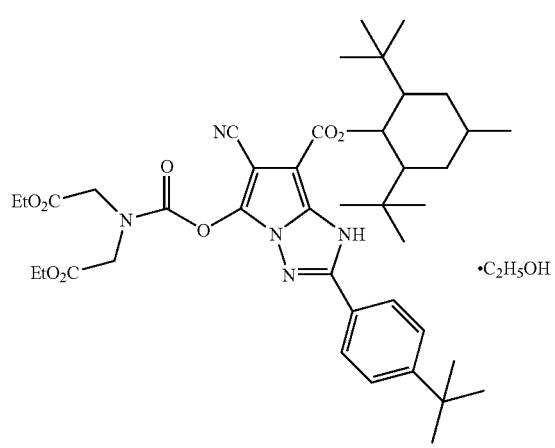
•C₂H₅OH

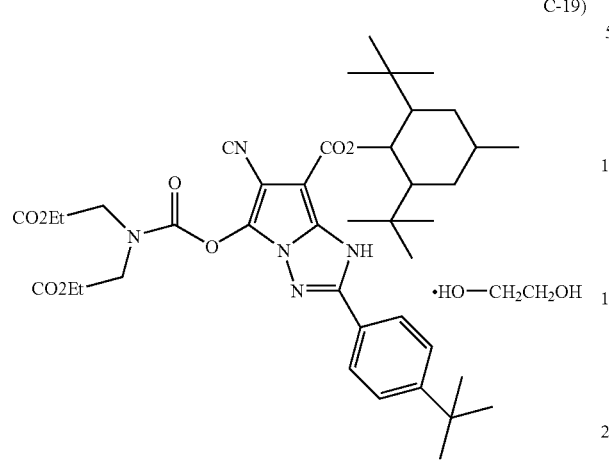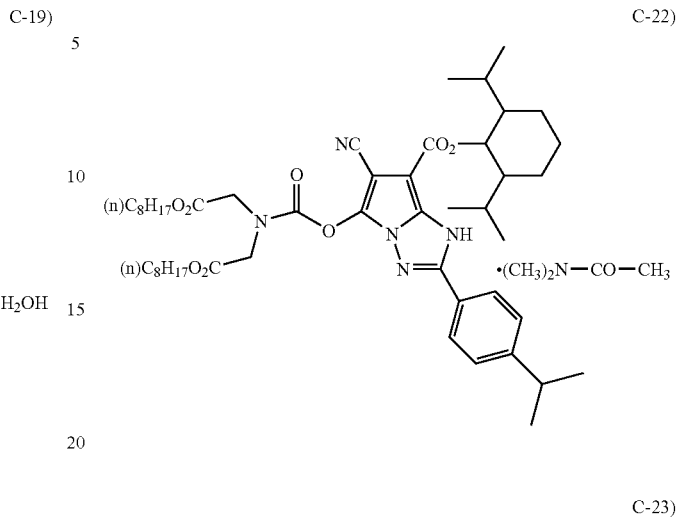

-continued
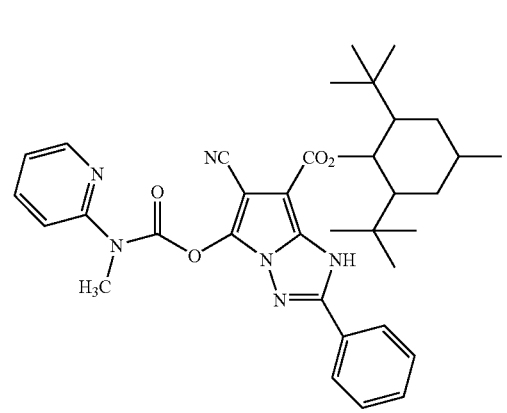
C-26)
·2Et₂O
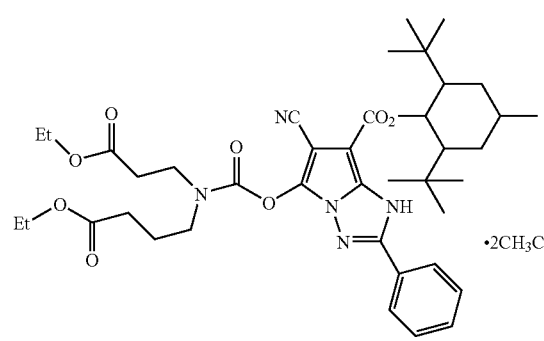
C-27)
·2CH₃CO₂Et
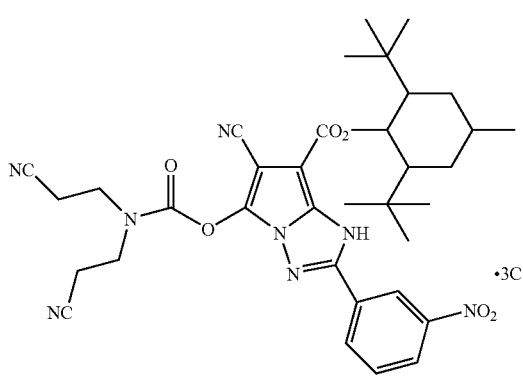
C-28)
·3CH₃CN
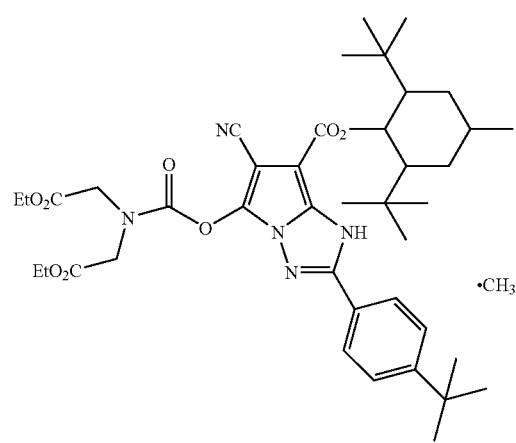
C-29)
·CH₃CO₂CH₃
-continued
C-30)
·
C-31)
·CH₃COCH₃
C-32)
·(CH₃)₂NCHO (I) or (II) is preferably applied are the silver halide color photosensitive materials described in JP-A No. 2002-174885, the disclosure of which is incorporated herein by reference.

4. Production Method

Next, a method of producing the compound of the invention will be explained. For producing the compound represented by the formula (I) or (II), reference may be made to the methods described in JP-A Nos. 8-109172 and 2004-123533, the disclosures of which are incorporated herein by reference.

Examples of a method of incorporating the above Org of the formula (I) or $R^{25}R^{26}R^{27}C$—OH of the formula (II) as a crystal solvent include a method in which pyrrolotriazole of the formula (I) or (II) is synthesized, then Org or $R^{25}R^{26}R^{27}C$—OH is allowed to coexist with the pyrrolotriazole independently or together with other solvents, and the system is put, as it is, in a condition (for example, a drop in temperature, a change of a solvent or a change in pH) where a product is precipitated and a method in which pyrrolotriazole of the formula (I) or (II) is synthesized, then treatments such as extraction and crystallization are carried out, then Org or $R^{25}R^{26}R^{27}C$—OH is allowed to coexist with the pyrrolotriazole, and the system is put, as it is, in a condition (for example, a drop in temperature, a change of a solvent or a change in pH) where a product is precipitated.

EXAMPLES

The present invention will be explained in more detail by way of examples. However, the invention is not intended to be limited thereby.

Example 1

The exemplified compound (C-14) was synthesized based on the following reaction scheme. Here, the compound (1) could be synthesized by referring to JP-A Nos. 11-199568 and 2004-123553, the disclosures of which ore incorporated herein by reference. The compound (2) was synthesized by referring to the method described in "J. Medicinal. Chem., 31, pp. 2277-2288 (1988)".

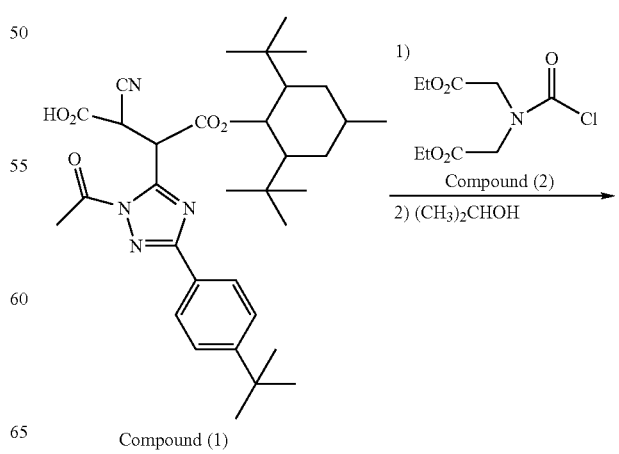

The compound represented by the formula (I) or (II) in the invention is used preferably as a synthetic intermediate of a dye or a dye forming coupler and particularly preferably as a dye forming coupler used in a silver halide color photosensitive material. This ensures that a silver halide photosensitive material improved particularly in color developing characteristics can be provided. The silver halide color photosensitive materials to which the compound represented by the formula -continued

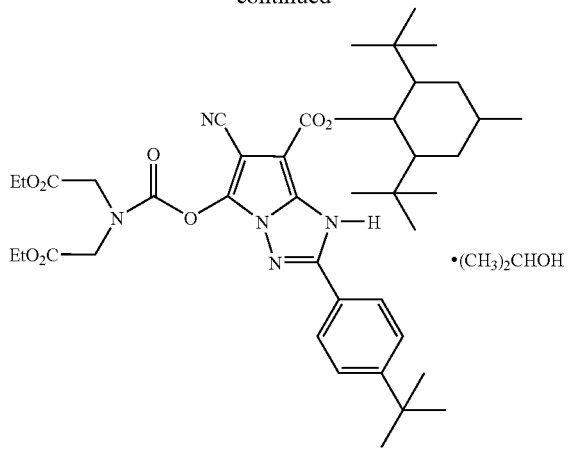

Exemplified compound (C-14)

A three-neck flask was charged with 55.07 g of the compound (1) and 250 ml of N,N-dimethylacetamide. 46.6 g of 4-methylpyridine was added dropwise to the mixture while stirring the mixture under ice-cooling over 30 minutes, followed by stirring for 1 hour, and 57.9 g of the compound (2) was further added dropwise to the mixture over 2 hours. The mixture was stirred, as it was, for 10 hours, and 500 ml of water, 100 ml of saturated brine and 500 ml of ethyl acetate were added to the mixture to carry out extraction. The resulting ethyl acetate phase was washed with an aqueous mixed solution of 400 ml of water and 100 ml of saturated brine five times. 500 ml of isopropyl alcohol was added to the residue obtained by concentrating the resulting ethyl acetate phase by using a rotary evaporator, and the mixture was stirred under ice-cooling. The precipitated crystals were filtered by suction filtration to obtain 71.1 g of the intended exemplified compound (C-14) (yield: 88%). The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 6 seconds.

NMR (CDCl$_3$): δ=11.15 (brs, 1H), 7.83 (d, J=8.7 Hz, 2H), 7.51 (d, J=8.7 Hz, 2H), 5.97(s, 1H), 4.2-4.4(m, 8H), 4.0-4.2 (m, 1H), 2.70 (d, J=5.1 Hz, 1H), 1.2-1.8 (m, 13H), 1.35 (s, 9H), 1.23 (d, J=6.3Hz, 6H), 1.08 (d, J=6.3Hz, 3H), 0.91 (s, 18H).

DSC: Measuring condition: Aluminum cell, heating speed=5.00° C./min., 147.78° C. (−24.51 J/g), 249.12° C. (−26.52 J/g)

Also, the obtained compound was found to contain isopropyl alcohol in a ratio by mol of 1:1 as a crystal solvent as a result of X-ray analysis as shown in FIG. 1.

Example 2

The exemplified compound (C-14) was synthesized according to the following method.

A three-neck flask was charged with 55.07 g of the above compound (1) and 250 ml of N,N-dimethylacetamide. 46.6 g of 4-methylpyridine was added dropwise to the mixture with stirring the mixture under ice-cooling over 30 minutes, followed by stirring for 1 hour, and 57.9 g of the compound (2) was further added dropwise to the mixture over 2 hours. The mixture was stirred, as it was, for 10 hours, and 500 ml of water, 100 ml of saturated brine and 500 ml of ethyl acetate were added to the mixture to carry out extraction. The resulting ethyl acetate phase was washed with an aqueous mixed solution of 400 ml of water and 100 ml of saturated brine five times. 40 ml of toluene and 300 ml of isopropyl alcohol were added to the residue obtained by concentrating the resulting ethyl acetate phase by using a rotary evaporator, and the mixture was then heated to dissolve the residue. 100 ml of water was added dropwise to the resulting solution to obtain crystals, which were then separated by suction filtration to obtain 76.8 g of the intended exemplified compound (C-14) (yield: 95%). The resulting compound was identified by NMR, DSC and X-ray analysis in the same manner as in Example 1.

The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 7 seconds.

Example 3

The exemplified compound (C-5) was synthesized according to the following reaction scheme. The following compound (3) was synthesized by referring to the method described in "J. Medicinal. Chem., 31, pp. 2277-2288 (1988)".

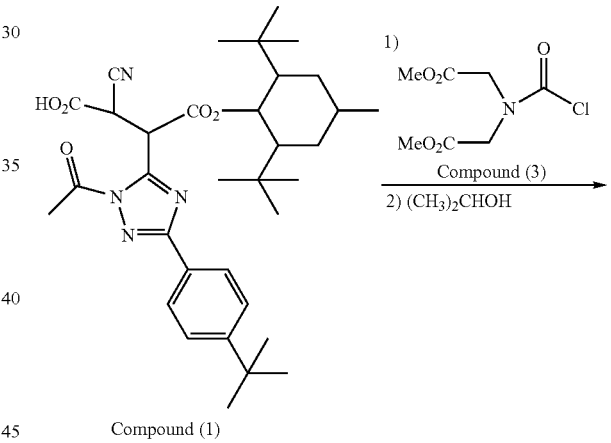

Compound (1)

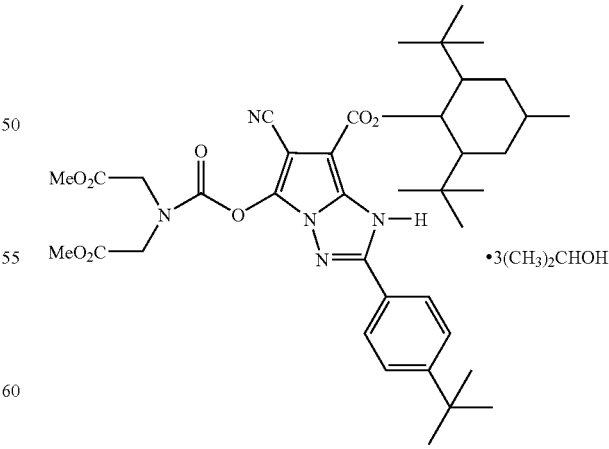

Exemplified compound (C-5)

A three-neck flask was charged with 55.07 g of the compound (1) and 250 ml of N,N-dimethylformamide. 47.4 g of pyridine was added dropwise to the mixture with stirring the mixture under ice-cooling over 30 minutes, followed by stirring for 1 hour, and 57.9 g of the compound (3) was further added dropwise to the mixture over 2 hours. The mixture was stirred, as it was, for 7 hours, and 500 ml of water, 100 ml of saturated brine and 500 ml of ethyl acetate were added to the mixture to carry out extraction. The resulting ethyl acetate phase was washed with an aqueous mixed solution of 400 ml of water and 100 ml of saturated brine five times. The residue obtained by concentrating the resulting ethyl acetate phase by using a rotary evaporator was purified by silica gel column chromatography. 450 ml of isopropyl alcohol and 20 ml of ethyl acetate were added to the purified residue and the mixture was then stirred under ice-cooling. The resulting crystals were then separated by suction filtration to collect 82.8 g of the intended exemplified compound (C-5) (yield: 92%). The resulting compound was identified by NMR, DSC and X-ray analysis in the same manner as in Example 1.

The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 7 seconds.

Comparative Example 1

A compound which was similar to the exemplified compound (C-14) but contained no crystal solvent was synthesized in the same manner as in Example 1 except that the crystallization method was changed. A three-neck flask was charged with 55.07 g of the compound (1) and 250 ml of N,N-dimethylacetamide. 46.6 g of 4-methylpyridine was added dropwise to the mixture with stirring the mixture under ice-cooling over 30 minutes, followed by stirring for 1 hour, and 57.9 g of the compound (2) was further added dropwise to the mixture over 2 hours. The mixture was stirred, as it was, for 10 hours, and 500 ml of water, 100 ml of saturated brine and 500 ml of ethyl acetate were added to the mixture to carry out extraction. The resulting ethyl acetate phase was washed with an aqueous mixed solution of 400 ml of water and 100 ml of saturated brine five times. 500 ml of methanol was added to the residue obtained by concentrating the resulting ethyl acetate phase by using a rotary evaporator, followed by stirring under ice-cooling. The precipitated crystals were then collected by suction filtration to obtain 65.8 g (yield: 88%) of the compound which was similar to the exemplified compound (C-14) but contained no crystal solvent. It was confirmed from the NMR data shown below that the resulting compound had no crystal solvent.

The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 71 seconds.

NMR (CDCl$_3$): δ=10.31 (brs, 1H), 7.80 (d, J=8.7 Hz, 2H), 7.51 (d, J=8.7 Hz, 2H), 5.96(s, 1H), 4.2-4.4(m, 8H), 1.2-1.8 (m, 13H), 1.35 (s, 9H), 1.08 (d, J=6.3 Hz, 3H), 0.91 (s, 18H).

Comparative Example 2

A compound which was similar to the exemplified compound (C-14) (Compound (F) in the following scheme) but contained no crystal solvent was synthesized using the method described in Example 2 of JP-A No. 2004-123553.

The method described in Example 1 of JP-A No. 2004-123553 is as follows.

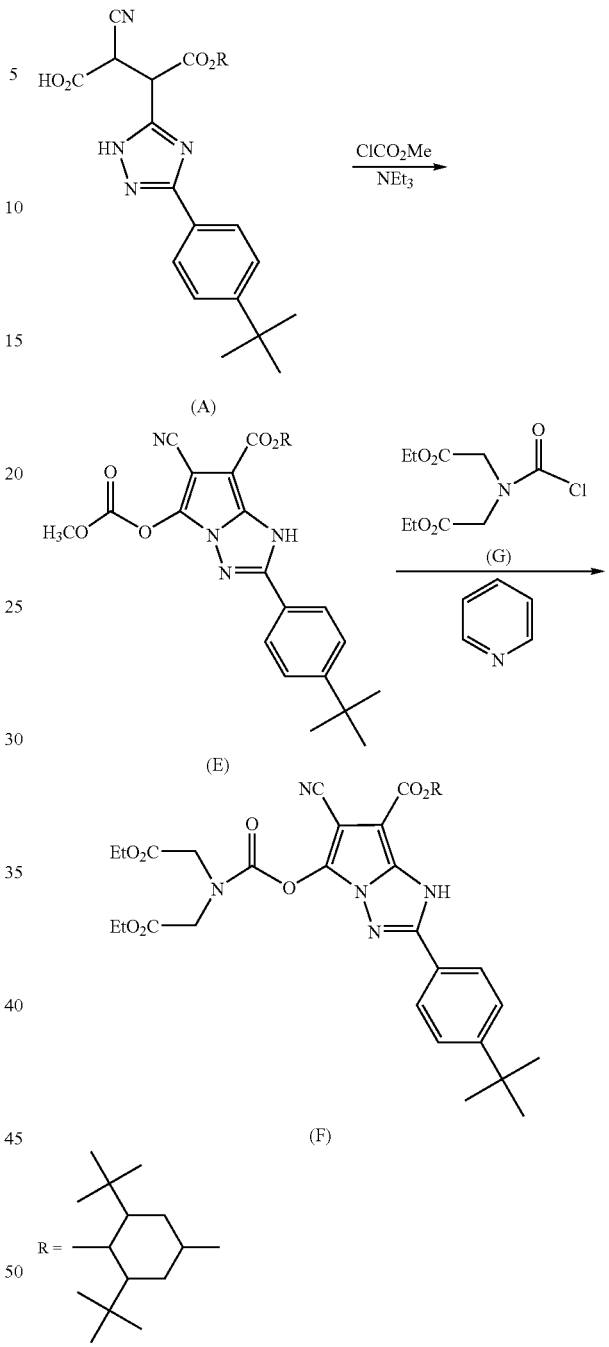

In this example, the amount of the compound (A) described in Example 1 of JP-A No. 2004-123553 was changed to 54.6 g from 10 g to undergo synthesis. Specifically, 54.6 g (100 mmol) of the compound (A) obtained by the above scheme was dissolved in 440 ml of toluene and the mixture was ice-cooled. 16.4 ml (211 mmol) of methyl chloroformate, 30.6 ml (219.4 mmol) of triethylamine were added dropwise in this order to the mixture. After the mixture was stirred under ice-cooling for 1 hour, it was raised to ambient temperature to measure quantitatively by HPLC, to find that the compound (E) was produced at a reaction rate of 100% in a yield of 95%.

The reaction solution of the compound (E) obtained in the above reaction was ice-cooled and 30.6 g (122 mmol) of the compound (G) was added to the reaction solution, to which was then added dropwise 18 ml (223 mmol) of pyridine. The mixture was raised to ambient temperature just after the dropwise addition was finished to react for further 1 hours. Then, 164 ml of water, 54.6 ml of concentrated hydrochloric acid and 273 ml of ethyl acetate were added to the reaction mixture to undergo phase separation. The organic layer was washed with 491 ml of 1 N hydrochloric acid and 491 ml of water in this order twice. After solvents were distilled under reduced pressure, the residue was recrystallized from 273 ml of methanol. The obtained crystals were collected by suction filtration to obtain 66.0 g (yield: 88%) of white crystals of the intended compound (F).

The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 80 seconds.

It was confirmed from the NMR data shown below that the resulting compound had no crystal solvent.

NMR (CDCl$_3$): δ=10.31 (brs, 1H), 7.80 (d, J=8.7 Hz, 2H), 7.51 (d, J=8.7 Hz, 2H), 5.96(s, 1H), 4.2-4.4(m, 8H), 1.2-1.8 (m, 13H), 1.35 (s, 9H), 1.08 (d, J=6.3 Hz, 3H), 0.91 (s, 18H).

Comparative Example 3

A compound which was similar to the exemplified compound (C-5) (Compound (C) in the following scheme) but contained no crystal solvent was synthesized using the method described in Example 1 of JP-A No. 2004-123553.

The method described in Example 1 of JP-A No. 2004-123553 is as follows.

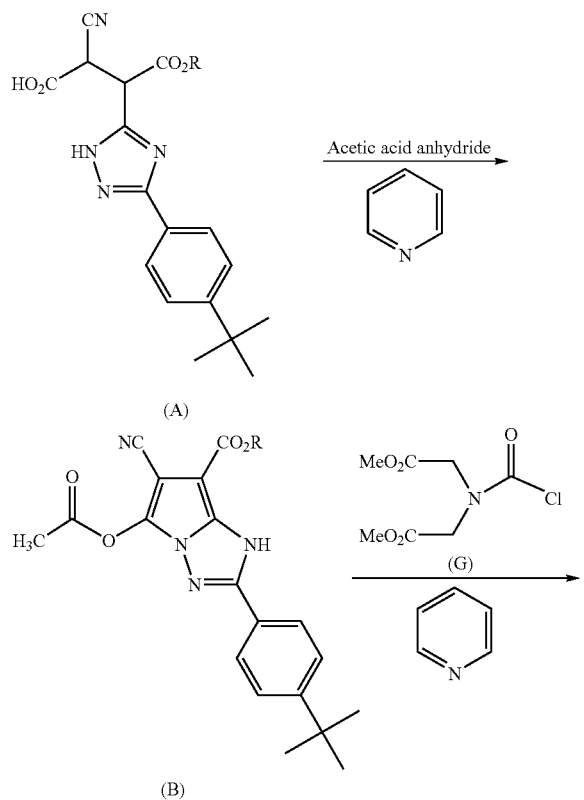

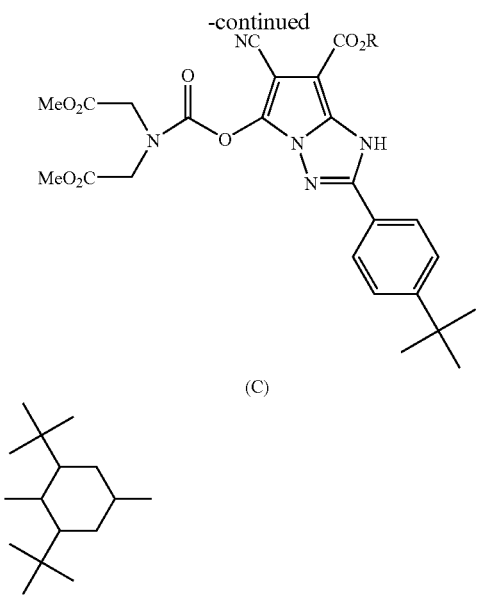

In this example, the amount of the compound (A) described in Example 1 of JP-A No. 2004-123553 was changed to 54.6 g from 10 g to undergo synthesis. Specifically, 54.6 g (100 mmol) of the compound (A) obtained by the above scheme was dissolved in 218 ml of toluene, 164 ml of N,N-dimethylacetamide and the mixture was ice-cooled. 20.7 ml (220 mmol) of acetic acid anhydride and in succession, 18 ml (223 mmol) of pyridine were added dropwise in this order to the mixture. After the mixture was reacted under ice-cooling for 1.5 hours, it was raised to ambient temperature to measure quantitatively by HPLC, to find that the compound (B) was produced at a reaction rate of 100% in a yield of 98%.

The reaction solution of the compound (B) obtained in the above reaction was ice-cooled and 28.4 g (122 mmol) of the compound (D) was added dropwise to the reaction solution, to which was then added dropwise 18 ml (223 mmol) of pyridine. The mixture was raised to 50° C. just after the dropwise addition was finished to react for further 2 hours. Then, 27.8 ml (200 mmol) of triethylamine were added to the reaction mixture to react for further 1 hour. After the reaction mixture was cooled to ambient temperature, 164 ml of water, 54.6 ml of concentrated hydrochloric acid and 273 ml of ethyl acetate were added to the reaction mixture to undergo phase separation. The organic phase was washed with 491 ml of 1 N hydrochloric acid and 491 ml of water in this order twice. After solvents were distilled under reduced pressure, the residue was recrystallized from a mixed solvent of 218 ml of methanol and 65.5 ml of ethyl acetate. The obtained crystals were collected by suction filtration to obtain 56.2 g (yield: 76%) of white crystals of the intended compound (C).

The filtering conditions at this time were as follows. A filter paper (11 cm) (trade name: ADVANTEC, manufactured by Toyo Roshi) was used in an 11 cm Nutche, reduced pressure at the time of suction was 40.0 hp, and time required for filtration was 85 seconds. It was confirmed from the NMR data shown below that the resulting compound had no crystal solvent.

Comparative Example 4

72.0 g of the exemplified compound 1 described in JP-A No. 2002-174885 was synthesized by the method described in Example 1 of this publication. The method described in Example 1 of JP-A No. 2002-174885 is as follows.

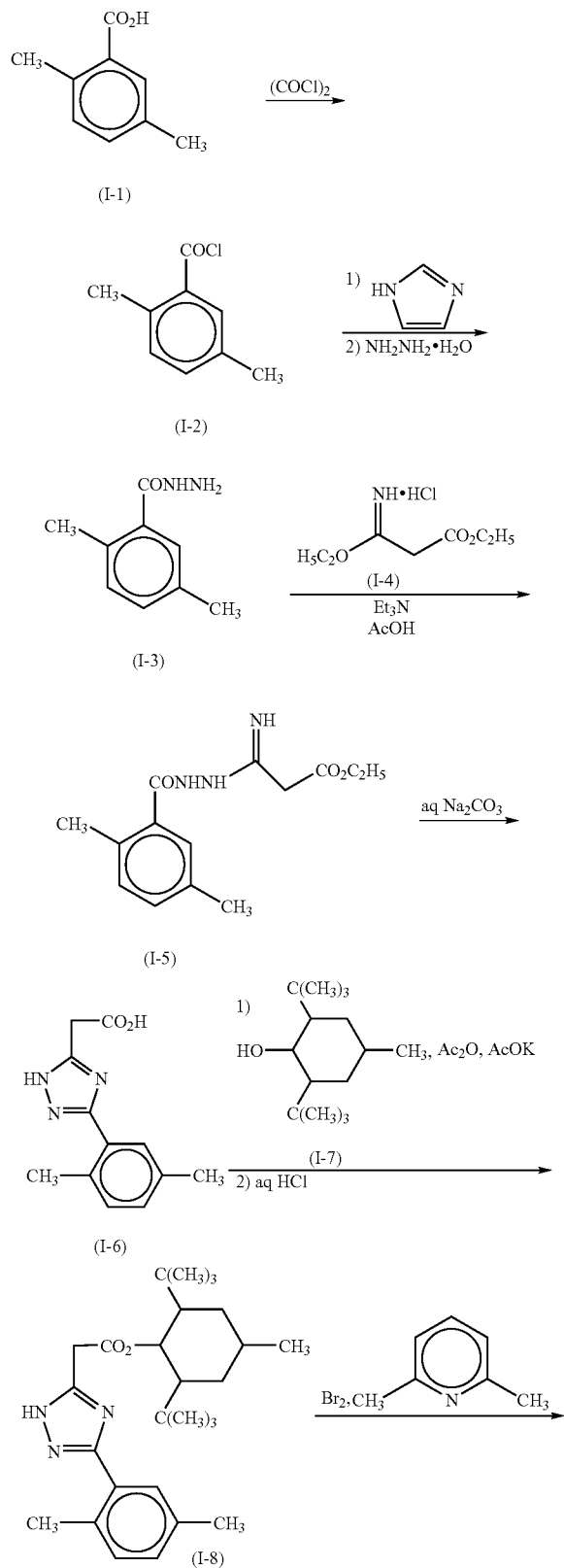

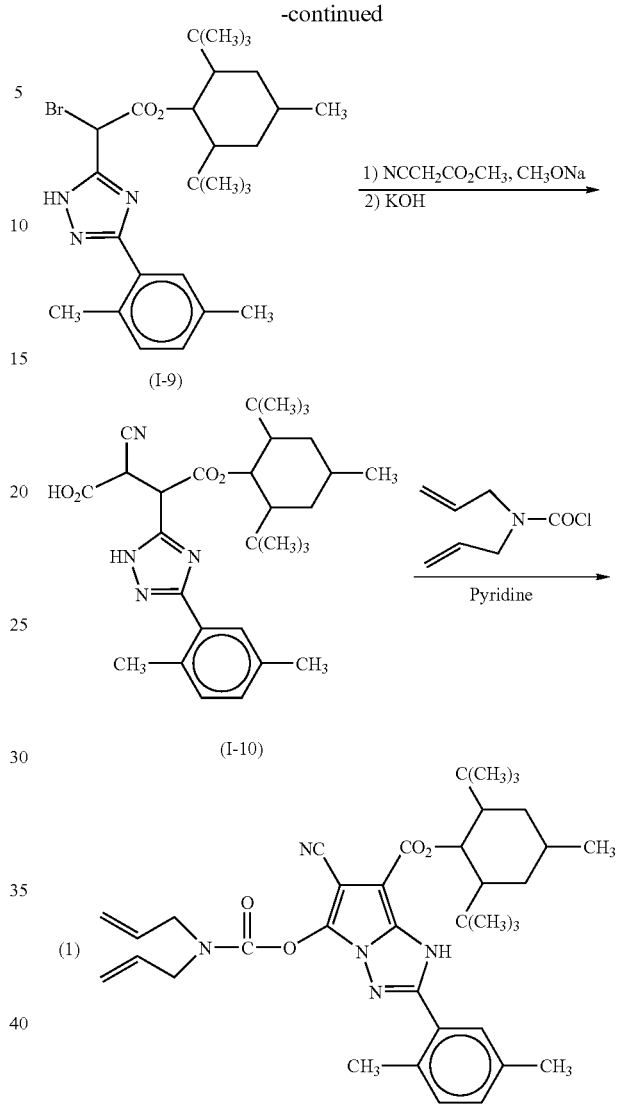

55 ml of oxalyl chloride was added dropwise to a solution prepared by dissolving 75.54 g of the synthetic compound (I-1) of the intermediate (I-2) in 300 ml of ethyl acetate, at ambient temperature with stirring. After the dropwise addition was finished, the stirring was further continued at ambient temperature for 1 hour. A solvent was removed to obtain 84.8 g (yield: 100%) of the intended intermediate (I-2) as an oily product.

A solution prepared by dissolving 102.7 g of synthetic imidazole of an intermediate (I-3) in 1.5 l of acetonitrile was ice-cooled. 84.8 g of the aforementioned intermediate (I-2) was added dropwise to the solution with keeping an internal temperature of 10° C. or less and stirring. After the dropwise addition was finished, the stirring was further continued for 1 hour. 73.3 ml of a hydrazine monohydrate was added dropwise to the reaction mixture with keeping an internal temperature of 10° C. or less. After the dropwise addition was finished, the ice bath was taken off and the reaction mixture was stirred at ambient temperature for 2 hours. 1 l of water was added to the reaction mixture and then, acetonitrile was distilled under reduced pressure. The precipitated crystals were collected by filtration and washed with water. The crystals were dried to thereby obtain 75.2 g (yield: 91%) of the intended intermediate (I-3) as white crystals.

16.2 ml of triethylamine was added to a mixture prepared by suspending 21.7 g of a synthetic compound (I-4) of an intermediate (I-5) in 600 ml of acetonitrile at ambient temperature with stirring. After the resulting mixture was stirred for 30 minutes, 15.2 g of the above intermediate (I-3) and 2.6 ml of acetic acid were added to the mixture one by one. After the mixture was reacted for 10 hours, 1 l of water was added, followed by further stirring the mixture under ice-cooling. The precipitated crystals were collected and washed with water. The obtained crystals were dried to obtain 18.3 g (yield: 71%) of the intended intermediate (I-5) as white crystals.

21.3 g of sodium carbonate anhydride was added to a mixture prepared by suspending 18.6 g of a synthetic intermediate (I-5) of an intermediate (I-6) in 100 ml of water and the mixture was heated with stirring on a steam bath. After the reaction was run for 2 hours, the reaction solution was cooled to ambient temperature and then poured into a mixture of ice-water and 35 ml of concentrated hydrochloric acid with stirring. The precipitated crystals were collected and washed with water. The obtained crystals were dried to obtain 14.5 g (yield: 93%) of the intended intermediate (I-6) as white crystals.

12.3 g of potassium acetate and 29.5 ml of acetic acid were added one by one to a mixture obtained by suspending 14.2 g of a synthetic compound (I-7) of an intermediate (I-8) and 14.4 g of the above intermediate (I-6) in 60 ml of ethyl acetate and the mixture was stirred at 45° C. for 3 hours on a hot-water bath to react. After that, the reaction mixture was ice-cooled and 50 ml of water was added to separate the organic phase. Solvents were removed from the organic phase and 100 ml of acetonitrile and 6.2 ml of concentrated hydrochloric acid were added to the residue. The mixture was reacted at 50° C. for 2 hours on a hot-water bath. The reaction mixture was allowed to be cooled to ambient temperature and 100 ml of water was added to the reaction mixture. The precipitated crystals were collected and washed with water. The obtained crystals were dried to obtain 23.3 g (yield: 85%) of the intended intermediate (I-8) as white crystals.

6.67 ml of 2,6-lutidine was added to a solution prepared by dissolving 22.9 g of the above synthetic intermediate (I-8) of an intermediate (I-9) in 250 ml of ethyl acetate, at ambient temperature with stirring. 2.82 ml of bromine was added dropwise to the mixture. After the dropwise addition was finished, the mixture was continuously stirred at ambient temperature for 1 hour and then, 100 ml of water was added. The organic phase was separated and washed with water and saturated brine in this order. After the organic phase was dried by magnesium sulfate anhydride, solvents were distilled to obtain 27.0 g (yield: 100%) of the intended intermediate (I-9) as an oily product.

A solution obtained by dissolving 25.7 ml of a synthetic sodium methoxide 28% methanol solution of an intermediate (I-10) in 60 ml of N,N-dimethylacetamide was ice-cooled and 11.5 ml of methyl cyanoacetate was added dropwise with keeping an internal temperature of 10° C. or less. After the mixture was stirred for 30 minutes as it was, 27.0 g of the above intermediate (I-9) was added to the mixture gradually. After the addition was finished, the mixture was stirred for 30 minutes and an aqueous solution obtained by dissolving 9.0 g of potassium hydroxide in 20 ml of water was added. The reaction mixture was stirred at 50° C. on a hot bath for 3 hours. After the reaction was completed, the reaction solution was poured into ice-water in which 15 ml of concentrated acid was dissolved. The reaction solution was extracted with ethyl acetate and the organic phase was washed with water and saturated brine one by one. The organic phase was dried by magnesium sulfate anhydride and then solvents were distilled to obtain 27.1 g (yield: 100%) of the intended intermediate (I-10) as an oily product.

27.1 g of the above synthetic intermediate (I-10) of the exemplified compound (1) was dissolved in 50 ml of N,N-dimethylacetamide to obtain a solution, to which 21 ml of pyridine and 18.3 g of diallylcarbamoyl chloride were added in this order. The mixture was reacted at ambient temperature for 12 hours. After the reaction was completed, the reaction mixture was poured into dilute hydrochloric acid. This mixture was extracted with ethyl acetate and the organic phase was washed with water. The precipitated crystals were collected by filtration and washed with water and saturated brine in this order. The organic phase was dried by magnesium sulfate anhydride and solvents were distilled. The residue was purified by silica gel column chromatography to obtain 19.4 g (yield: 59%) of the intended exemplified compound (1).

It was confirmed from NMR data that the obtained exemplified compound (1) contained no crystal solvent.

Comparative Example 5

The compounds III-1a to f and compounds III-3a to 3n described in JP-A No. 8-109172 were synthesized according to the method described in Synthetic Example 1 or 2 of the publication.

The methods described in Synthetic Examples 1 and 2 of JP-A No. 8-109172 are as follows.

Synthesis Example 1

According to the following schemes, Compounds (I-1), (II-1), and (III-1) were synthesized.

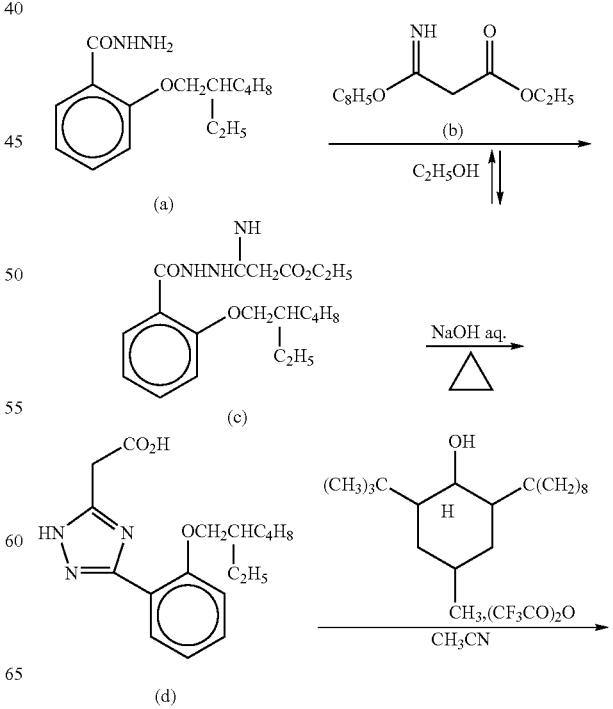

scheme V

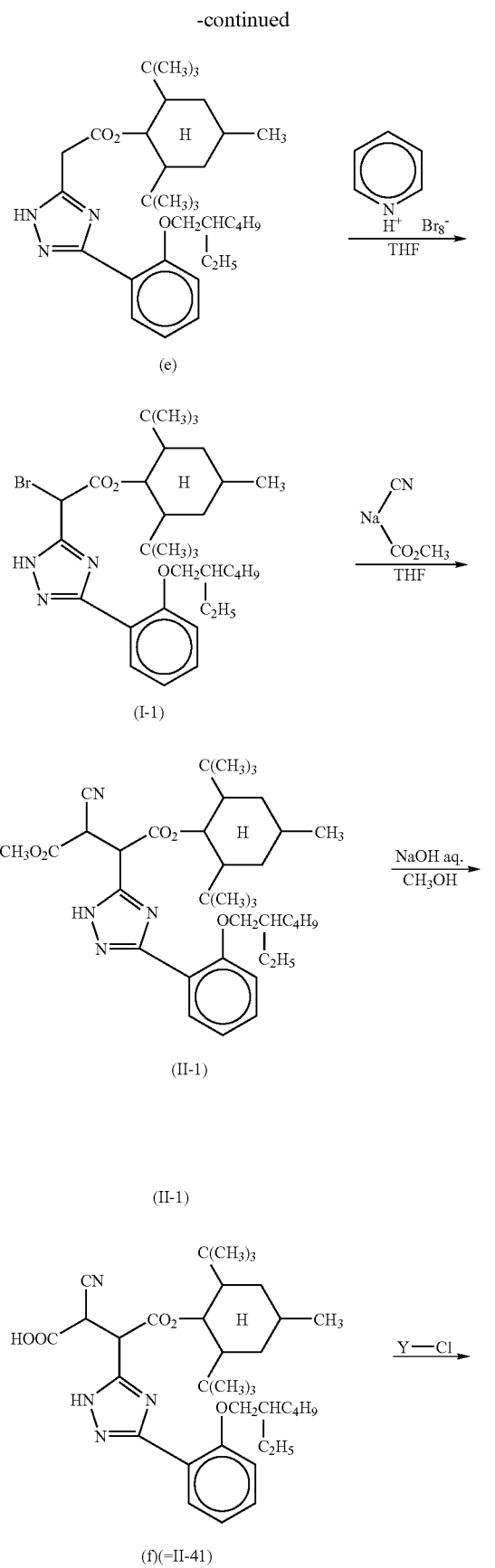

(e)

(I-1)

(II-1)

(II-1)

(f)(=II-41)

-continued

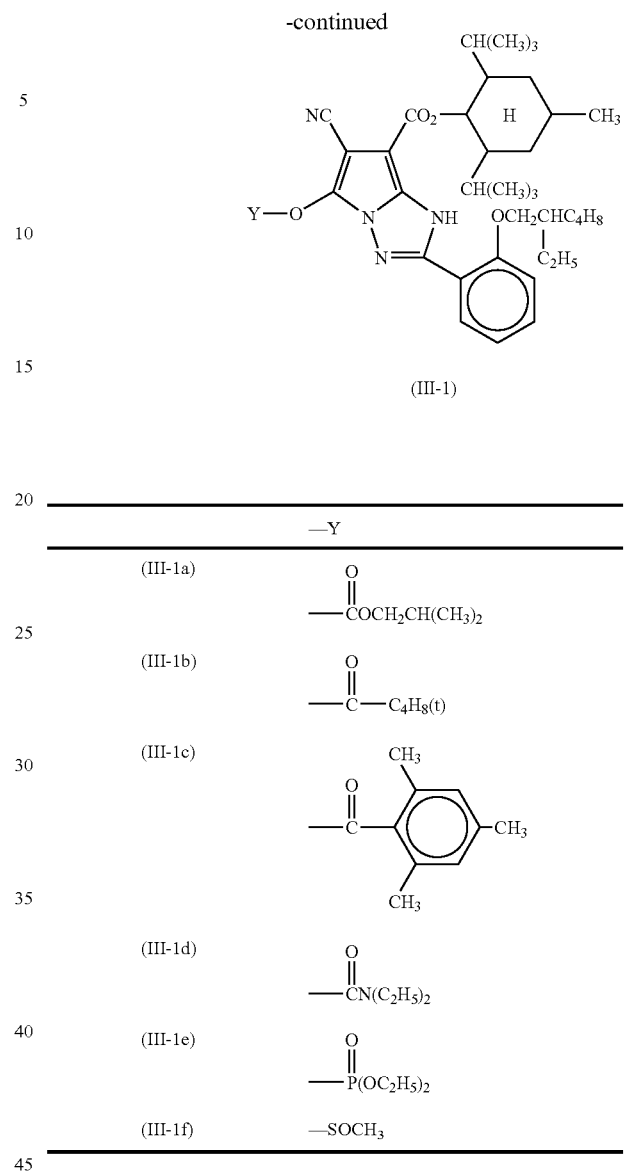

(III-1)

| | —Y |
|---|---|
| (III-1a) | —COCH$_2$CH(CH$_3$)$_2$ (with C=O) |
| (III-1b) | —C(=O)—C$_4$H$_8$(t) |
| (III-1c) | —C(=O)—(2,4,6-trimethylphenyl) |
| (III-1d) | —C(=O)N(C$_2$H$_5$)$_2$ |
| (III-1e) | —P(=O)(OC$_2$H$_5$)$_2$ |
| (III-1f) | —SOCH$_3$ |

<<Synthesis of Compound (d)>>

A mixture of o-2-ethylhexyloxybenzhydrazide (a) (40 g, 151 mmol) and ethyl cyanoacetate imidate (b) (25 g, 155 mmol) was stirred in 100 ml of ethanol with refluxing for 5 hours. The ethanol was distilled off under a reduced pressure. To the residue was added 350 ml of an aqueous solution of sodium hydroxide (12.2 g, 306 mmol). After this mixture was stirred with refluxing for 2 hours, 31 ml of concentrated hydrochloric acid was added to the reaction mixture. This reaction mixture was extracted with 200 ml of ethyl acetate. The organic phase was washed with water and dried with sodium sulfate. The solvent was then distilled off under a reduced pressure. The residue was recrystallized from an ethyl acetate/hexane mixture (1:1) to obtain Compound (d) (20 g, 60.4 mmol; 40%).

<<Synthesis of Compound (e)>>

To a solution in 200-ml acetonitrile of 2,6-di-t-butyl-4-methylcyclohexanol (17 g, 75 mmol) was added dropwise trifluoroacetic anhydride (10.6 ml, 75 mmol) at 0° C. Subsequently, Compound (d) (20 g, 60.4 mmol) was gradually added thereto. After the reaction mixture was stirred at room temperature for 2 hours, 300 ml of water was added. This reaction mixture was extracted with 300 ml of ethyl acetate. The organic phase was washed with aqueous sodium bicarbonate solution, water, and aqueous common salt solution. The washed organic phase was dried with sodium sulfate, and then concentrated under a reduced pressure. The residue was purified by column chromatography to obtain Compound (e) (18.5 g, 34.3 mmol; 57%).

<<Synthesis of Compound (I-1)>>

Pyridinium bromide perbromide (12.0 g, 37.7 mmol) was added to a tetrahydrofuran solution of Compound (e) (18.5 g, 34.3 mmol) at room temperature. This mixture was stirred for 8 hours. A solution in water (200 ml) of sodium sulfite (2 g) was added to the reaction mixture, which was then extracted with 300 ml of ethyl acetate. The organic phase was washed with water and aqueous common salt solution, dried with sodium sulfate, and then concentrated under a reduced pressure. The resulting residue was purified by column chromatography to obtain Compound (I-1) (16.0 g, 25.9 mmol; 75%; melting point, 132-133° C.).

<<Synthesis of Compound (II-1)>>

To a solution in 50-ml tetrahydrofuran of methyl cyanoacetate (7.2 g, 73 mmol) was gradually added 60% sodium hydride (12.4 g, 60 mmol) at 0° C. This mixture was stirred at room temperature for 30 minutes (Solution S1). Solution S1 was added dropwise to a solution in tetrahydrofuran (75 ml) of Compound (I-1) (15.0 g, 24.3 mmol) at 0° C. This mixture was stirred at room temperature for 1 hour. Thereafter, 200 ml of 1 N hydrochloric acid and 200 ml of ethyl acetate were added to the reaction mixture to conduct extraction. The organic phase was washed with water and aqueous common salt solution, dried with sodium sulfate, and then concentrated under a reduced pressure. The resulting residue was purified by column chromatography to obtain Compound (II-1) as a light-yellow amorphous solid (12.7 g, 19.9 mmol; 82%). From its NMR spectrum, this Compound (II-1) was found to be a mixture of two isomers.

<<Synthesis of Compound (f)>>

Aqueous sodium hydroxide solution (5 g of NaOH and 50 ml of water) was added to a solution in 100-ml methanol of Compound (II-1) (10.5 g, 16.5 mmol). This mixture was stirred at 50° C. for 2 hours. Thereafter, 200 ml of 1 N hydrochloric acid and 200 ml of ethyl acetate were added to the reaction mixture to conduct extraction. The organic phase was washed with water and aqueous common salt solution, and dried with sodium sulfate. The solvent was then distilled off under a reduced pressure. Subsequently, 100 ml of hexane was added to the resulting oil, upon which the oil crystallized. The crystals were recovered by filtration, and dried to obtain Compound (f) (=II-41) (9.5 g; 92%; melting point, 175-177° C.).

<<Synthesis of Compound (III-1a)>>

Isobutyl chloroformate (0.5 ml, 3.85 mmol) was added dropwise to a solution in 10-ml ethyl acetate of Compound (f) (0.80 g, 1.28 mmol) at 0° C. Subsequently, triethylamine (0.55 ml, 3.85 mmol) was added thereto dropwise. After this mixture was stirred at 0° C. for 15 minutes, 10 ml of 1 N hydrochloric acid was added. The organic phase was washed with water and aqueous common salt solution, and dried with sodium sulfate. The solvent was then distilled off under a reduced pressure. The residue was recrystallized from acetonitrile to obtain Compound (III-1a) (0.60 g, 67%).

<<Synthesis of Compound (III-1b)>>

Pivaloyl chloride (0.185 ml, 1.5 mmol) was added dropwise to a solution in 3-ml pyridine of Compound (f) (0.31 g, 0.5 mmol) at 0° C. After this mixture was stirred at room temperature for 2 hours, 10 ml of ethyl acetate and 10 ml of 1 N hydrochloric acid were added. The organic phase was washed with 1 N hydrochloric acid, water, and aqueous common salt solution, and dried with sodium sulfate. The solvent was then distilled off under a reduced pressure. The residue was recrystallized from acetonitrile to obtain Compound (III-1b) (0.15 g, 0.22 mmol; 44%).

<<Synthesis of Compound (III-1c)>>

1,3,5-Trimethylbenzoyl chloride (1.5 ml, 1.8 mmol) was added dropwise to a solution in 20-ml pyridine of Compound (f) (2.0 g, 3.18 mmol) at 0° C. After this mixture was stirred at room temperature for 5 hours, 100 ml of ethyl acetate and 100 ml of 1 N hydrochloric acid were added. The organic phase was washed with 1 N hydrochloric acid, water, and aqueous common salt solution, and dried with sodium sulfate. The solvent was then distilled off under a reduced pressure. The residue was recrystallized from acetonitrile to obtain Compound (III-1c) (1.6 g, 2.13 mmol; 67%).

<<Synthesis of Compound (III-1d)>>

Diethylcarbamyl chloride (1.0 ml, 1.8 mmol) was added dropwise to a solution in 20-ml pyridine of Compound (f) (2.0 g, 3.2 mmol) at 0° C. After this mixture was stirred at room temperature for 20 hours, 100 ml of ethyl acetate and 100 ml of 1 N hydrochloric acid were added. The organic phase was washed with 1 N hydrochloric acid, water, and aqueous common salt solution, and dried with sodium sulfate. The solvent was then distilled off under a reduced pressure. The residue was recrystallized from acetonitrile to obtain Compound (III-1d) (1.2 g, 1.7 mmol; 53%).

<<Synthesis of Compound (III-1e)>>

Diethylphosphonic acid chloride (1.1 ml, 1.8 mmol) was added dropwise to a solution in 30-ml ethyl acetate of Compound (f) (2.0 g, 3.18 mmol) at 0° C. Subsequently, triethylamine (1.15 ml, 1.8 mmol) was added thereto dropwise. After this mixture was stirred at room temperature for 4 hours, 30 ml of 1 N hydrochloric acid was added. The organic phase was washed with water and aqueous common salt solution, and dried with sodium sulfate. The solvent was then distilled off under a reduced pressure. The residue was recrystallized from acetonitrile to obtain Compound (III-1e) (1.3 g; 55%).

<<Synthesis of Compound (III-1f)>>

Methanesulfonyl chloride (1.0 ml, 12.9 mmol) was added dropwise to a solution in 30-ml pyridine of Compound (f) (3.0 g, 4.8 mmol) at 0° C. After this mixture was stirred at room temperature for 1 hour, 100 ml of ethyl acetate and 100 ml of 1 N hydrochloric acid were added. The organic phase was washed with 1 N hydrochloric acid, water, and aqueous common salt solution, and dried with sodium sulfate. The solvent was then distilled off under a reduced pressure. The residue was recrystallized from acetonitrile to obtain Compound (III-1f) (2.2 g, 3.22 mmol; 67%).

Synthesis Example 2

Synthesis of Compounds (I-3), (II-3) and (III-3)

Compound (g) was synthesized in the same manner as in Synthesis Example 1, and Compounds (I-3), (II-3), and (III-3) were synthesized therefrom according to the following scheme.

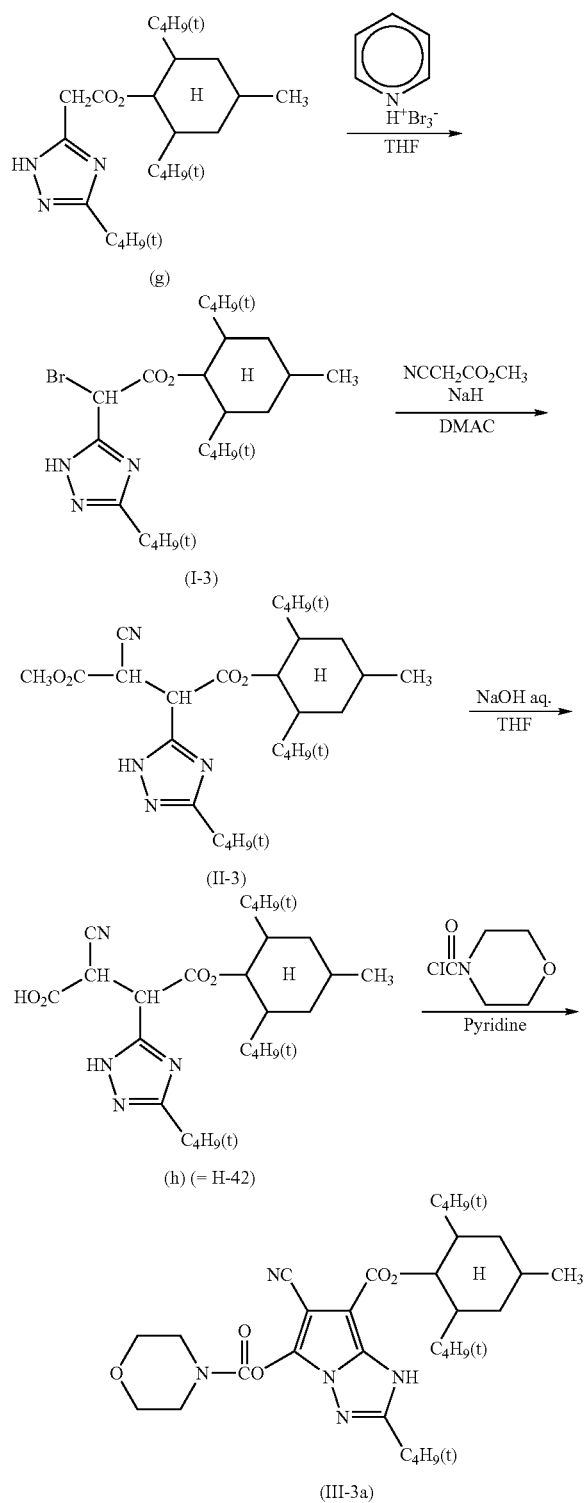

(g)

(I-3)

(II-3)

(h) (= H-42)

(III-3a)

<<Synthesis of Compound (I-3)>>

Pyridinium bromide perbromide (30 g, 93 mmol) was added to a solution in tetrahydrofuran (300 ml) of Compound (g) (28 g, 71.5 mmol) at room temperature. This mixture was stirred at room temperature for 10 hours. A solution in water (300 ml) of sodium sulfite (10 g) was added to the reaction mixture, and this mixture was stirred for further 2 hours. Ethyl acetate (500 ml) was added to the organic phase, which was then washed four times with a dilute aqueous solution of common salt. The washed organic phase was dried with sodium sulfate, and then concentrated under a reduced pressure. The residue was recrystallized from an ethyl acetate/hexane mixture to obtain Compound (I-3) (26.5 g, 56.3 mmol; 79%; melting point, 170-171° C.).

<<Synthesis of Compound (II-3)>>

To a solution in dimethylformamide (20 ml) of methyl cyanoacetate (2.5 g, 25 mmol) was gradually added 60% sodium hydride (0.83 g, 21 mmol) at 0° C. This mixture was stirred at room temperature for 15 minutes (Solution S2). Solution S2 was added dropwise to a solution in dimethylformamide (35 ml) of Compound (I-3) (4.7 g, 10 mmol) at 0° C. This mixture was stirred at room temperature for 1 hour. Thereafter, 100 ml of 1 N hydrochloric acid and 100 ml of ethyl acetate were added to the reaction mixture to conduct extraction. The organic phase was washed with water and aqueous common salt solution, dried with sodium sulfate, and then concentrated under a reduced pressure. The residue was purified by column chromatography to obtain Compound (II-3) as a light-yellow amorphous solid (3.9 g, 7.9 mmol; 79%). From its NMR spectrum, this Compound (II-3) was found to be a mixture of two isomers.

<<Synthesis of Compound (h)>>

Aqueous sodium hydroxide solution (4 g of NaOH and 30 ml of water) was added to a solution in tetrahydrofuran (30 ml) of Compound (II-3) (3.9 g, 7.9 mmol). This mixture was stirred at room temperature for 3 hours, and then poured into 100 ml of dilute hydrochloric acid. The resulting mixture was extracted with ethyl acetate, and the resulting organic phase was washed with water (three times) and dried with sodium sulfate. Thereafter, the solvent was distilled off under a reduced pressure to obtain 3.7 g of crude compound (h). This crude compound (h) was used as it was in the subsequent step without conducting further purification.

<<Synthesis of Compound (III-3a)>>

Morpholinocarbamoyl chloride (2.16 g, 14.4 mmol) was added dropwise to a solution in pyridine (20 ml) of 3.7 g of crude compound (h) at 0° C. After this mixture was stirred at room temperature for 2 hours, 100 ml of ethyl acetate and 100 ml of 1 N hydrochloric acid were added. The organic phase was washed with 1 N hydrochloric acid, water, and aqueous common salt solution, and dried with sodium sulfate. The solvent was then distilled off under a reduced pressure. The residue was recrystallized from an ethyl acetate/hexane mixture to obtain Compound (III-3a) [3.3 g, 5.8 mmol; 80% (based on the acid chloride)]. With respect to Compounds (III-3b) to (III-3n), the desired compounds were able to be obtained by the same method.

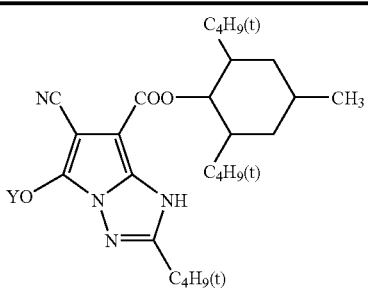

(III-3a) Y = 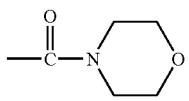

(III-3b) Y = 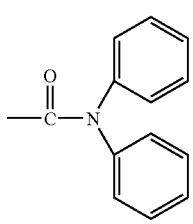

(III-3c) Y = 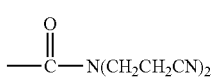

(III-3d) Y = 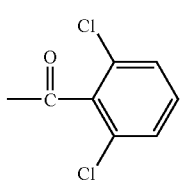

(III-3e) Y = 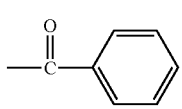

(III-3f) Y = 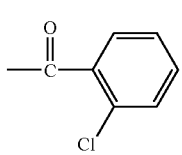

(III-3g) Y = 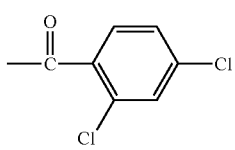

(III-3h) Y = 

(III-3j) Y = 

(III-3j) Y = 

(III-3k) Y = 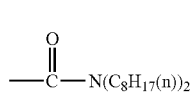

(III-3l) Y = 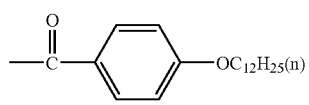

(III-3m) Y = 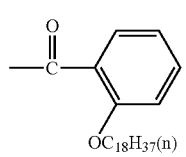

(III-3n) Y = 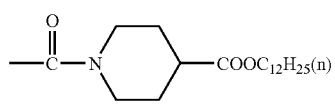

It was confirmed from NMR or DSC data that all the obtained compounds contained no crystal solvent.

What is claimed is:

1. A solvate crystal of a pyrrolotriazole compound having the following structure:

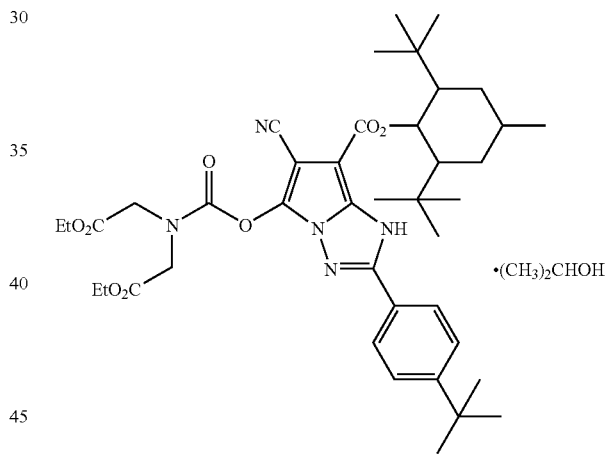

wherein the above crystal has a space group of $P2_1/n$ (#14) and an X-ray crystal structure characterized by lattice constants of a=18.574 Å (angstroms), b=15.077 Å, c=19.022 Å, β=118.311° and Z=4.

* * * * *